US010322235B2

(12) United States Patent
Thorne, Jr. et al.

(10) Patent No.: US 10,322,235 B2
(45) Date of Patent: Jun. 18, 2019

(54) MULTIPLE CHAMBER SYRINGE PISTON AND MIXING DEVICES

(71) Applicant: Thorne Consulting and Intellectual Property, LLC, Bountiful, UT (US)

(72) Inventors: Gale Harrison Thorne, Jr., Bountiful, UT (US); Kendall Patterick Thorne, Layton, UT (US); Gale Harrison Thorne, Sr., Bountiful, UT (US)

(73) Assignee: THORNE CONSULTING & INTELLECTUAL PROPERTY, LLC, Bountiful, UT (US)

( * ) Notice: Subject to any disclaimer, the term of this patent is extended or adjusted under 35 U.S.C. 154(b) by 405 days.

(21) Appl. No.: 15/282,774

(22) Filed: Sep. 30, 2016

(65) Prior Publication Data

US 2018/0093040 A1 Apr. 5, 2018

(51) Int. Cl.
*A61M 5/00* (2006.01)
*A61M 5/19* (2006.01)
*A61M 5/315* (2006.01)
*A61M 5/31* (2006.01)

(52) U.S. Cl.
CPC .......... *A61M 5/19* (2013.01); *A61M 5/31511* (2013.01); *A61M 5/31513* (2013.01); *A61M 2005/3128* (2013.01); *A61M 2005/31521* (2013.01)

(58) Field of Classification Search
CPC .................... A61M 5/178; A61M 5/31; A61M 2005/3128; A61M 5/19
USPC .......................................................... 604/191
See application file for complete search history.

(56) References Cited

U.S. PATENT DOCUMENTS

| 5,743,886 | A  | 4/1998 | Lynn et al. |
| 7,048,720 | B1 | 5/2006 | Thorne, Jr. et al. |
| 7,101,354 | B2 | 9/2006 | Thorne, Jr. et al. |
| 7,766,919 | B2 | 8/2010 | Delmotte |
| 7,789,862 | B2 | 9/2010 | Thorne, Jr. |

(Continued)

*Primary Examiner* — Jason E Flick
(74) *Attorney, Agent, or Firm* — Gale H. Thorne

(57) ABSTRACT

A plurality of embodiments of mixing syringes are provided. Inventive key to all of the embodiments is a piston valve which divides a barrel to create a pair of chambers in which matter and liquid can be disparately and securely disposed before mixing. Each disclosed piston valve is actuated by force on an associated plunger rod which produces pressure within an associated syringe resulting in a change of the valve state from closed to open. In addition, each such valve comprises check valve action which is permissive to only distal flow through the syringe. Embodiments for both a basic mixing syringe and a mixing syringe with flush are disclosed. Considerations and methods for chamber filling without valve actuation are provided. A mixing syringe system with flush system utilizing a dual chamber syringe having a male luer fitting and a separate diluent containing vessel having a female luer fitting is also disclosed. In addition, a valve piston which comprises a proximally disposed skirt for providing an additional seal when the valve piston momentarily cants is disclosed. Further a valve piston, which comprises a plurality of rings, at least one of which is forced to further radially displace by a positive pressure differential applied against one of two opposing convex piston faces to thereby increase a seal between barrel wall and piston is disclosed.

17 Claims, 14 Drawing Sheets

(56) References Cited

U.S. PATENT DOCUMENTS

| | | |
|---|---|---|
| 8,992,469 B2 | 3/2015 | Bartlett, II et al. |
| 2008/0208137 A1* | 8/2008 | Fago ................ A61M 5/31596 604/191 |
| 2013/0165853 A1 | 6/2013 | Kawamura |
| 2015/0343153 A1 | 12/2015 | Granelli et al. |

* cited by examiner

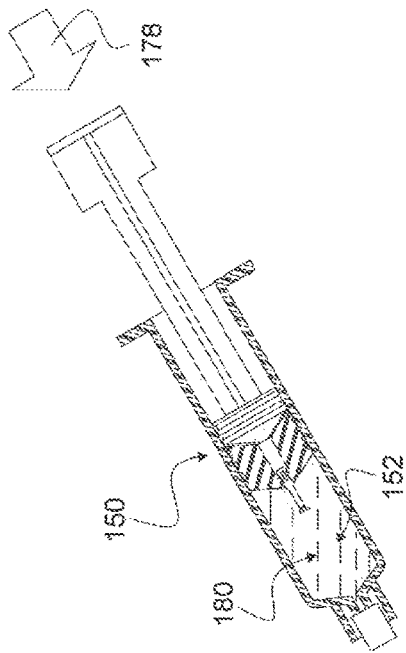
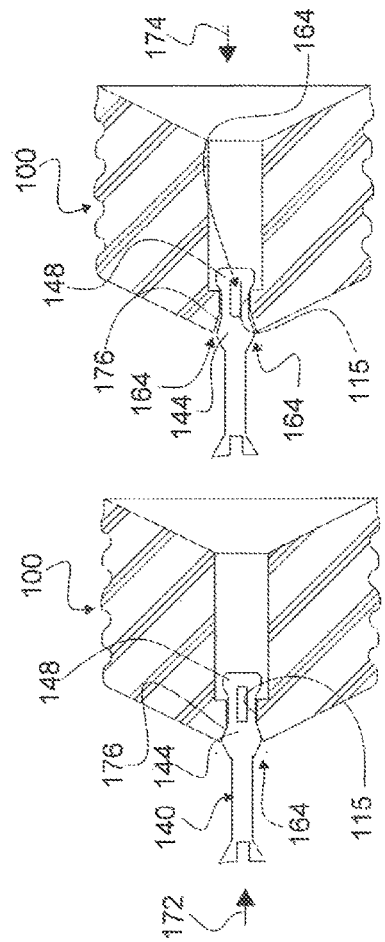
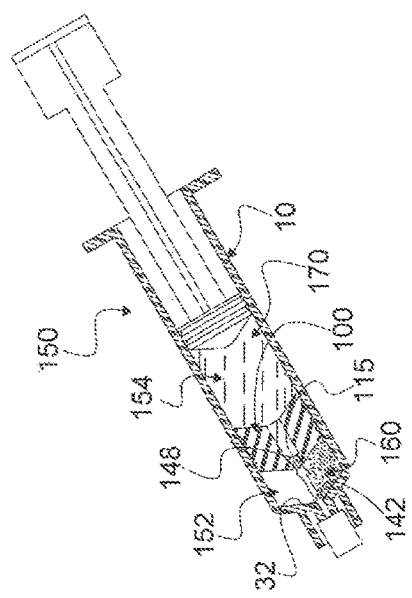

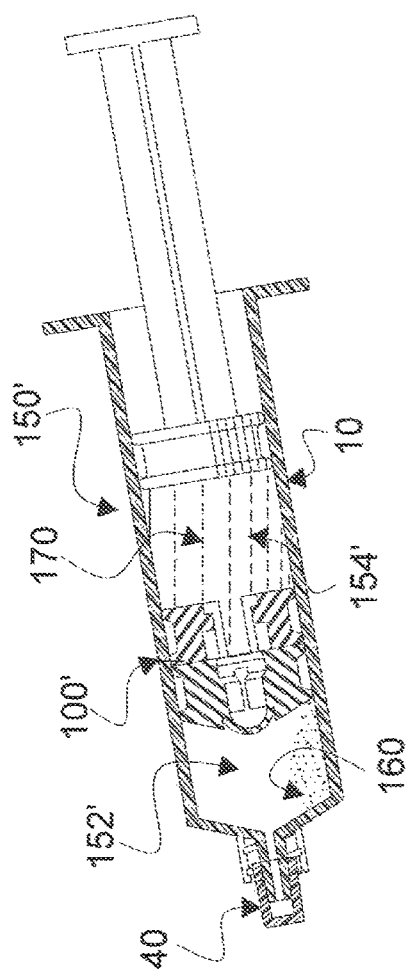
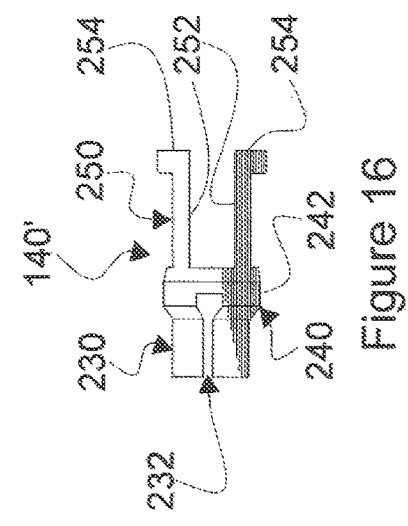
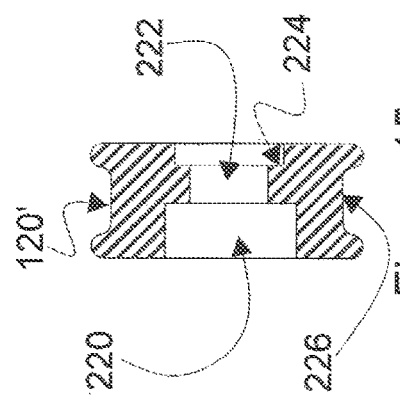
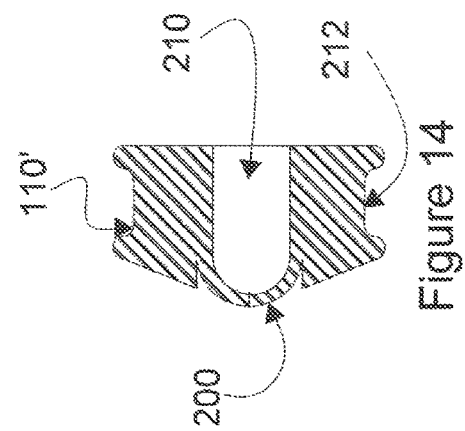

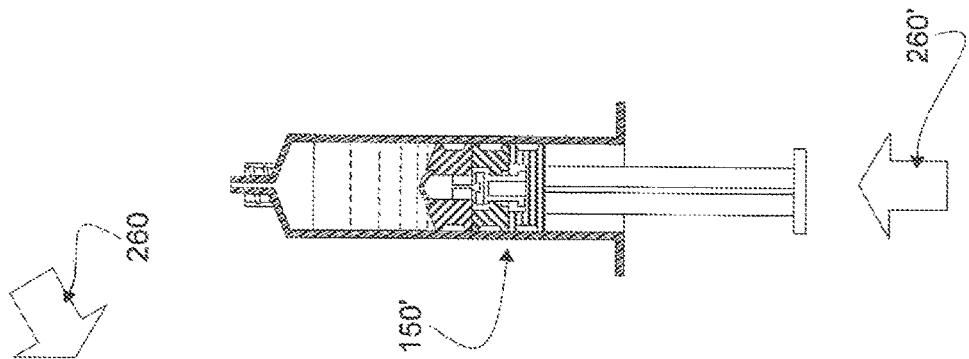
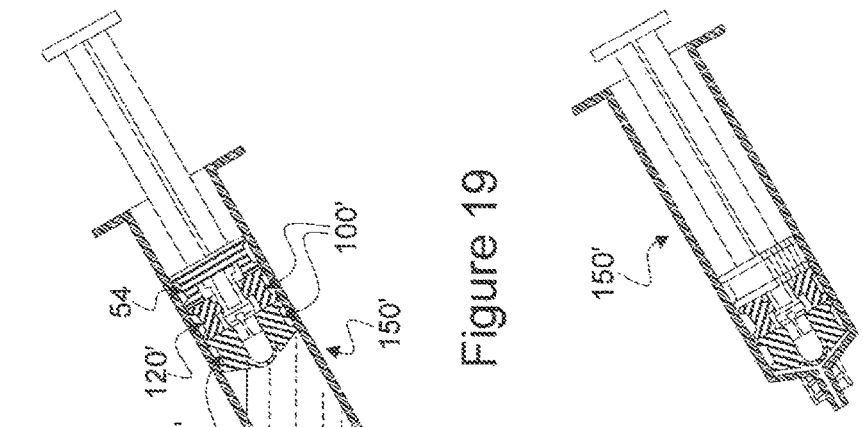
Figure 17  Figure 18  Figure 19  Figure 20  Figure 21

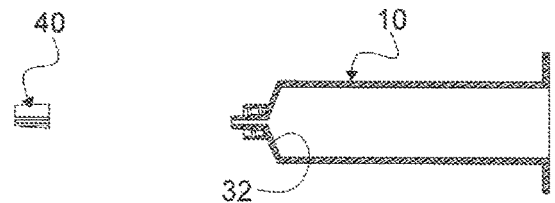
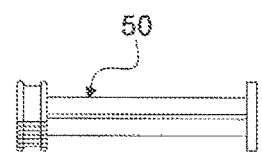
Figure 23    Figure 22    Figure 24
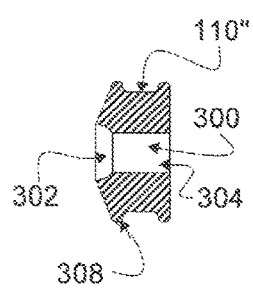
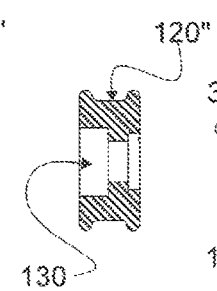
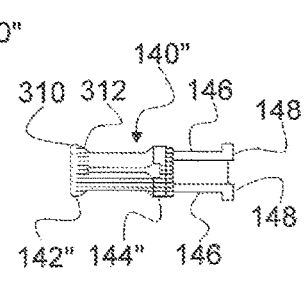
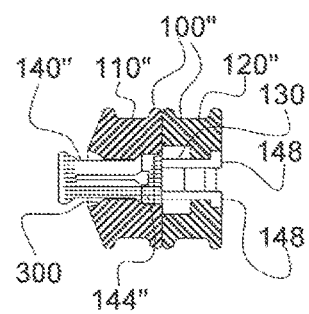
Figure 25    Figure 26    Figure 27    Figure 27A
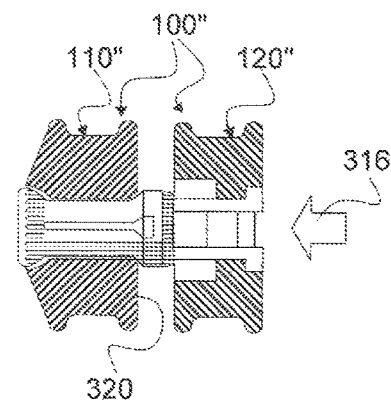
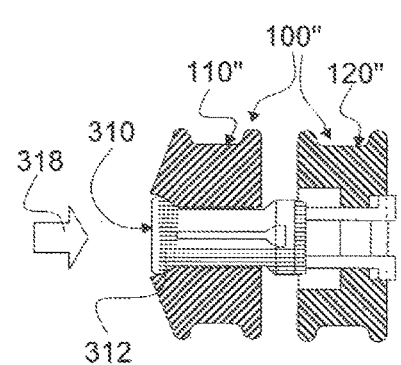
Figure 27B    Figure 27C

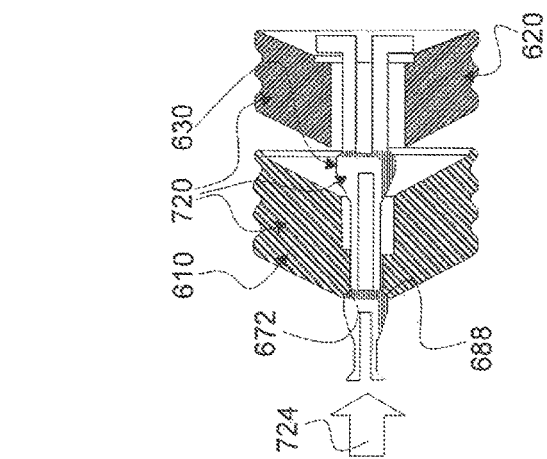
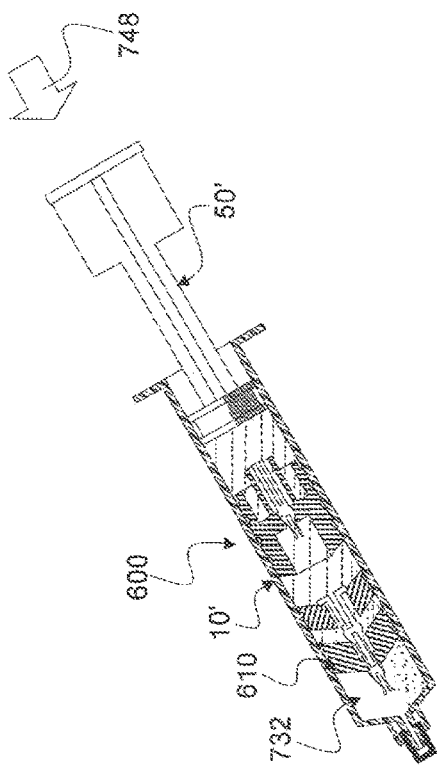
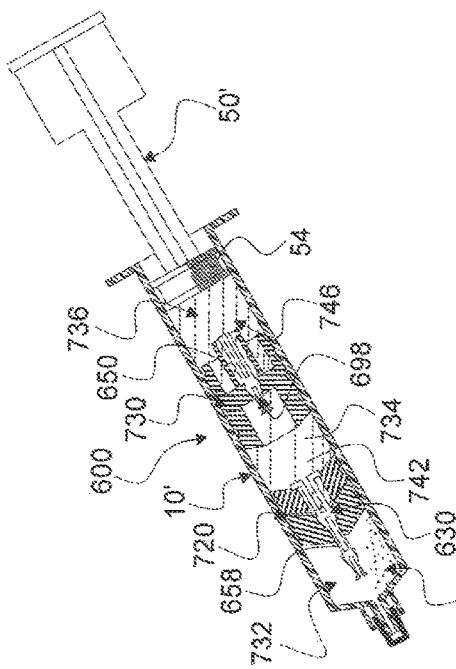
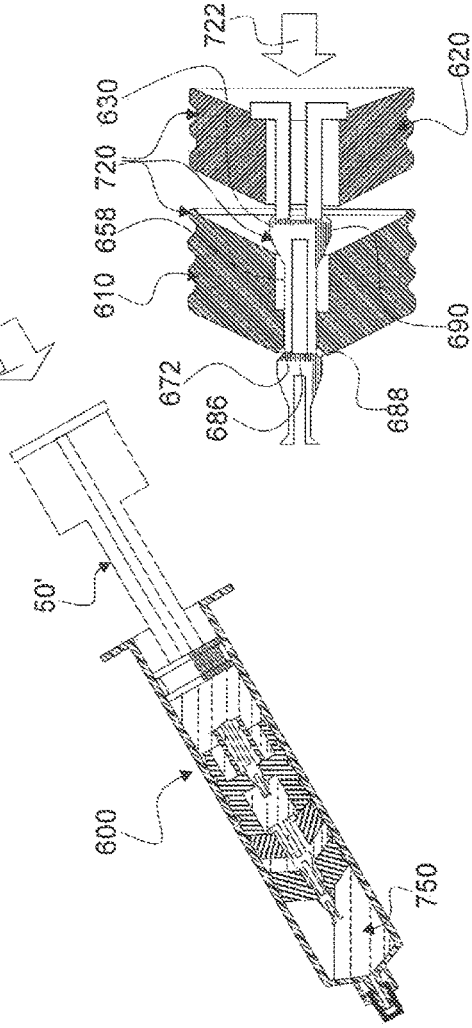
Figure 41A
Figure 41B
Figure 42
Figure 43
Figure 44

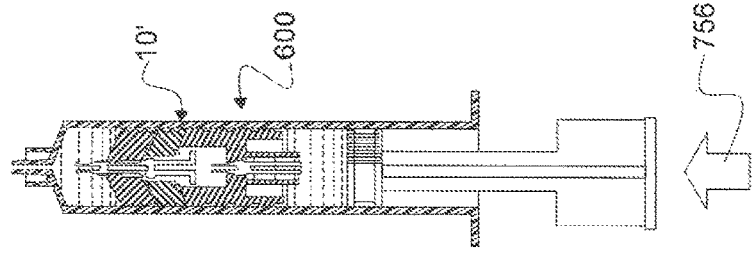
Figure 46
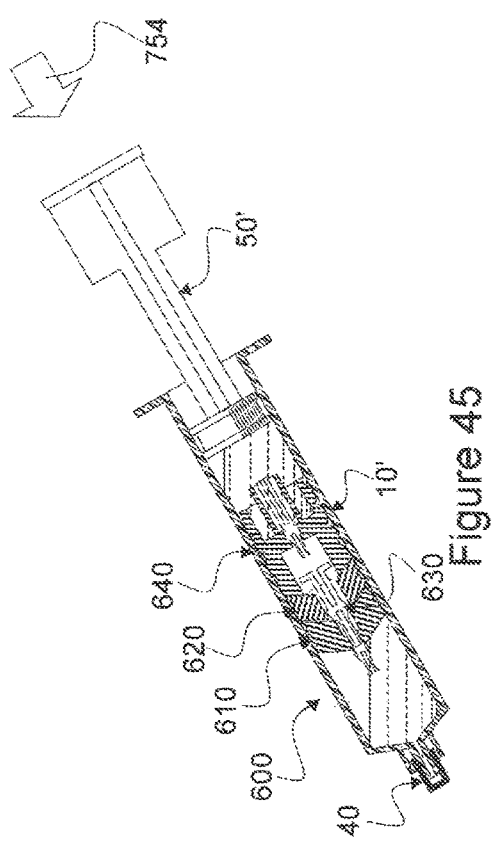
Figure 45
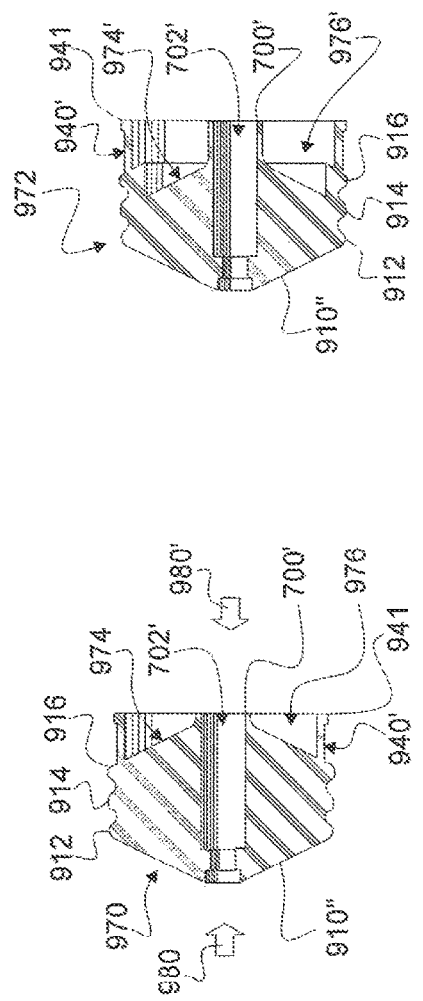
Figure 65
Figure 64

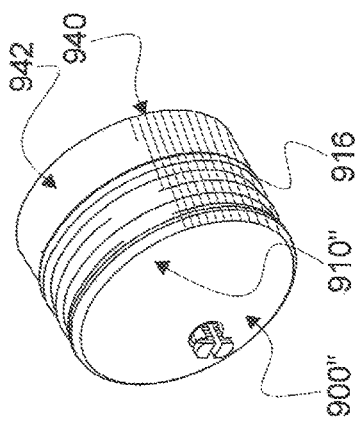
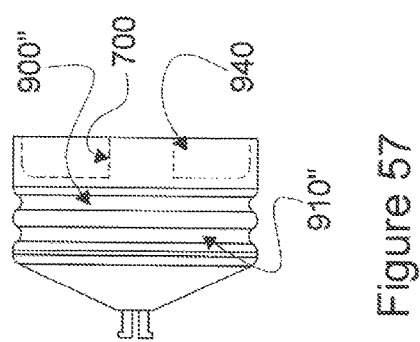
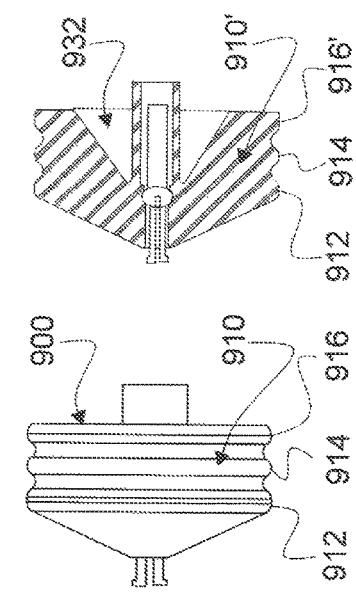
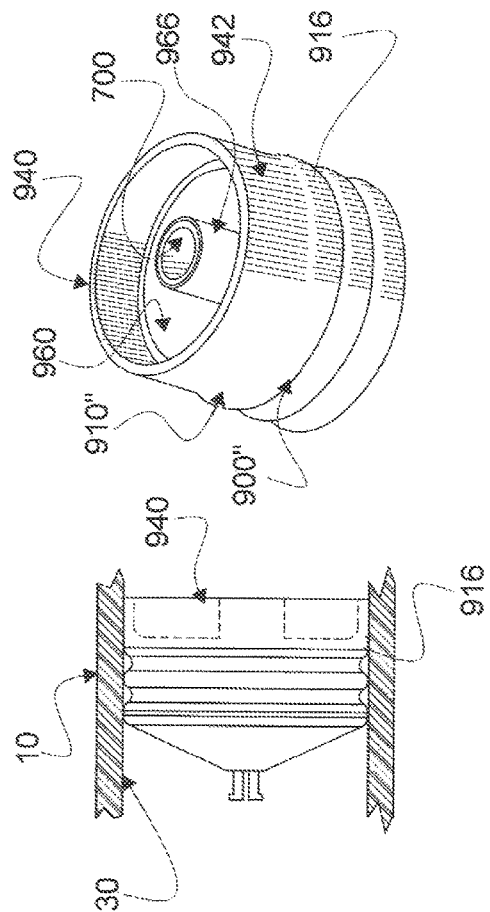
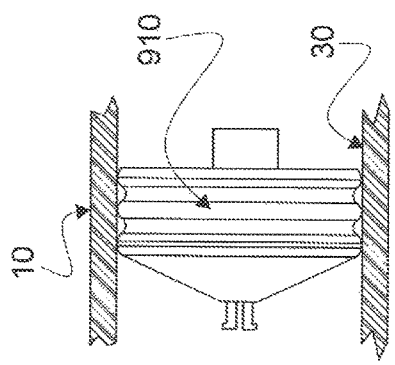

MULTIPLE CHAMBER SYRINGE PISTON AND MIXING DEVICES

CONTINUATION-IN-PART

This Patent Application is a Continuation-in-Part of U.S. patent application Ser. No. 14/921,343 (referenced hereafter as Thorne '343) titled DUAL-CHAMBER SYRINGE AND ASSOCIATED CONNECTING SYSTEMS and filed by Gale H. Thorne, Jr. et al. on Oct. 23, 2015 which is a Continuation-in-Part of U.S. patent application Ser. No. 14/121,681 filed Oct. 7, 2014 and titled COMPONENTS AND DEVICES FOR CLOSED MEDICAL SYSTEM OPERATION by Gale H. Thorne which is a Continuation-in-Part of U.S. patent application Ser. No. 13/872,828, filed Apr. 29, 2013 and titled TWISTED SLIT VALVE filed by Gale H. Thorne, now allowed as U.S. Pat. No. 9,295,827, and, further, a Continuation-in-Part of U.S. patent application Ser. No. 13/068,529 filed May 13, 2011 by Gale H. Thorne, et al. and titled PRESSURE ACTUATED VALVE FOR MULTI-CHAMBER SYRINGE APPLICATIONS now allowed as U.S. Pat. No. 9,289,562, contents of each of which are made part hereof, by reference.

FIELD OF INVENTION

This invention relates to mixing syringes and multi-chamber syringes and, in particular, to mixing syringes which utilize conventional syringe barrels and, in the case of multi-chamber flush syringes, dispense fluid from each chamber separately and sequentially. Inventions disclosed herein also relate directly to pistons which are displaced within a syringe barrel by pressure and force by direct communication with fluids, rather than being displaced by a rod structure (e.g. a syringe plunger rod).

DESCRIPTION OF RELATED ART

This invention is a Continuation-in-Part of Thorne '343 which discloses multi-chamber syringes which can be used for sequential delivery of fluids. As this instant invention can involve a combination of both a mixing syringe and a sequential fluid delivery application, contents of Thorne '343 are included herein by reference.

Syringes for storing and mixing materials comprising diluents in one chamber and either dry (e.g. lyophilized) or liquid reagents (e.g. medications) in a disparate chamber are well known. Such syringes provide a means for mixing, while both materials are kept disparate within the syringe prior to use. Achieving a mixing syringe in current art has taken many forms, including frangible diaphragms, special barrel geometries which permit fluid flow between chambers when a separating stopper is displaced to a predetermined slotted or expanded portion of a barrel, telescoping barrels and plugs. Often some type of special barrel design is utilized. Beyond the requirement for special barrel design, there may be performance issues associated with such syringes, such as dead space and numbers of mixing syringe parts and complexity.

As an example, U.S. Pat. No. 4,041,945 titled MIXING SYRINGE and issued to Aeneus C. Guiney Aug. 16, 1977 (Guiney) discloses mixing syringe apparatus which employs a conventional syringe barrel. One chamber for a diluent is disposed in the syringe barrel. A chamber for material to be diluted is disposed in a chamber formed in a resilient piston head. It is noted that such a mixing syringe limits volume of material which can be diluted and establishes a dead space relative to a delivered volume.

Generally, within each serial delivery syringe, chambers are separated by an intermediate sliding stopper or other part which receives motive force communicated through an intermediate fluid from a primary stopper which is part of a plunger assembly and against which an external force is applied. For disparate fluids to be dispensed sequentially or serially, each intermediate stopper must provide a fluid-tight seal to assure that no inadvertent chamber-to-chamber communication occurs and that all fluid from a distal chamber is evacuated from the syringe before dispensing fluid from a more proximal chamber. Once the distal chamber of the syringe is so purged, that intermediate stopper must be breached or bypassed to permit dispensing of the contents of a proximal or intermediate chamber.

U.S. Pat. No. 7,101,354 (now abandoned), titled MIXING SYRINGE WITH AND WITHOUT FLUSH and issued to Thorne, jr. et al. Sep. 5, 2006 (Thorne '354) discloses a mixing syringe with and without flush disposed in a conventional medical syringe barrel. In the case of a simple mixing syringe, a slit valve is disposed between a chamber containing dose material and gas and a chamber containing diluting material.

While such a slit valve is effective in keeping the dose material and diluent disparate as long as a pressure differential across the slit valve is insufficient to cause fluid communication across the valve, such valves are generally subject to opening with a small positive pressure exerted across the slit valve from the diluent chamber toward the dose chamber. Such a combination creates a significant likelihood for inadvertent premature delivery of diluent into the dose chamber and, thus, invalidating the dose material prior to planned mixing. For this reason, while Thorne '354 provides an effective method for dispensing diluent into a dose chamber for mixing, there is no safety provision for assuring diluent dispensing does not occur prematurely eliminating commercial use enablement.

Definition of Terms

Following is a brief list of clarifying definitions for terms used in this Application:

assembly n: a device which is made from at least two interconnected parts barrel n: a hollow, elongated cylindrical portion of a syringe which is conventionally open on one end to receive a piston and plunger rod used for displacing fluid within the barrel and partially closed at an opposite end except for an orifice through which fluid is ejected or aspirated bi-stable adj: a descriptor for a device having two stable states conventional adj: sanctioned by general custom; i.e. commonplace, ordinary blow-by n: a condition, whereby fluid is displaced across rings of a syringe piston disposed within a syringe barrel, which either contests or foils the disparate state of material separated by the piston chamber n: a volumetric portion of a divided barrel disparate n: when used in conjunction with a liquid volume, a volume of liquid which is distinctly separate from another liquid volume differential pressure ($\Delta P$) n: a pressure gradient resulting from unequal pressures exerted upon opposing sides of a structure; generally as used herein, $\Delta P = P_p - P_d$ (P definitions hereafter)

distal adj: a term which depicts placement away from a reference point (e.g. away from a user of a syringe)
downstream adj: a direction which is consistent with flow out of a syringe or away from a user
fluid n: a substance (e.g. a liquid and/or gas) which tends to take the shape of a container
front adj/n: distally disposed or a distally disposed site (e.g. a front of a syringe comprises the dispensing orifice)
gas n: a fluid which is not a liquid and which fills surrounding space
liquid n: a fluid which is neither solid nor gaseous, generally considered to be free flowing like water
liquid only zone n: a space within a chamber, which contains both gas and liquid, in which only liquid can reside due to gravitational attraction and state differences between gas and liquid
medial adj: occurring away from an outer edge; disposed near the center of (e.g. disposed away from an edge or periphery and in the vicinity of a center of gravity or axis of symmetry)
$P_d$ n: pressure in a distal chamber or a pressure which is distally disposed relative to a structure across which a differential pressure is effected
piston n: a displaceable part used in the barrel of a syringe, e.g. a syringe plunger apparatus, a part affixed to a syringe plunger rod by which a user applies force to displace fluid within a syringe barrel
prime v: to purge gas from a cavity such that remaining fluid is only liquid
$P_p$ n: pressure in a proximal chamber or a pressure which is proximally disposed relative to a structure across which a differential pressure is effected
proximal adj: opposite of distal (e.g. a term which depicts placement nearer than a reference point)
rear adj: opposite from front (i.e. generally associated with a part of a syringe barrel which is proximal to a syringe user)
reflux n: a type of undesired retrograde (upstream) flow of liquid (e.g. blood into a catheter or the like) from a vessel in which the catheter or the like resides
rod n: a part of a rear plunger assembly of a syringe, e.g. a syringe plunger rod
state n: mode or condition of being; when referenced to a valve assembly, a condition which permits or restricts fluid flow under predetermined conditions; state may also reference a material state (e.g. gas, liquid or solid)
stiction n: a special case of friction; stiction being the force required to initiate motion to a resting body, esp. when stiction is greater than moving friction
stem n: an elongated part which can be displaced to open a valve, e.g. a piston valve
stop n: an obstruction which is differentiated from friction or stiction, esp. an obstruction which halts displacement of a stopper or piston
substantially adv: to a large or main degree (e.g. something that is substantially round [with little defect] is considered round, but that must be considered as in effect, as nothing physical is perfect)
syringe n: a device used for injecting or withdrawing fluids
upstream adj: a direction which is against the direction of flow from a syringe (opposite of downstream)
valve piston n: a valve part associated with displacing fluid in a syringe

BRIEF SUMMARY AND OBJECTS OF THE INVENTION

In brief summary, embodiments of novel inventions disclosed herein alleviate all known problems related to providing an effective mixing syringe assembly within a conventional syringe barrel and to displacing a fluid-driven piston within a barrel while keeping material on both sides of the piston disparate. Within the scope of invention, a mixing syringe assembly and multi-chamber, sequential dose dispensing syringe combination can be provided either with or without a self-contained flush.

Generally, embodiments according to the instant invention employ a syringe having a barrel of conventional (traditional) design which is hollow, having an elongated internal, substantially constant diameter cylindrical surface, the barrel comprising an open proximal end and a distal end having a closed interior about an orifice through which fluid is transferred. Of course, during mixing, a cap about the orifice is used to keep chambers within the barrel enclosed. A plunger rod and piston combination is disposed within the barrel to accomplish fluid displacement and dispensing by application of external force.

Mixing Syringes

Key to the instant invention of a mixing syringe is a means for keeping material disposed within the barrel of the syringe disparate until a predetermined act is performed, that act being definitive and sufficiently assertive to assure no inadvertent, unwanted and/or premature mixing occurs. However, by performance of such an act, open fluid pathways are provided for communicating fluids for mixing.

Examples of three embodiments of simple mixing syringes according to the instant invention are provided hereafter. In addition, two embodiments of mixing syringes with flush according to the instant invention are provided in a section thereafter.

Simple Mixing Syringes

A first embodiment of a simple mixing syringe comprises a plunger valve which further comprises a displaceable stem. The stem is similar to the stem disclosed in Thorne '343, but rather comprises a pair of bulbous sections, the first of which interacts within a through hole in a valve plunger to, until the stem is displaced, close and keep material in a front chamber disparate from material in a rear chamber. A predetermined volume of gas is provided resident in the front chamber.

To open the valve to provide a pathway for displacement of liquid in the rear chamber into the front chamber, with the cap in place, the plunger valve is displaced, by compressive force (pressure) by the syringe plunger rod, until a portion of the stem collides with the front interior surface of the syringe barrel. It should be noted that such displacement within the barrel compresses the gas in the front chamber until the segment of the stem collides with the dispensing end of the syringe. Such gas compression requires action and force which assures performance of a definite, assertive act to open the plunger valve.

Once the plunger valve is opened, displacement of the valve plunger ceases and a fluid pathway is opened between the front and rear chambers. To displace liquid initially disposed in the rear chamber into the front chamber, a pumping process comprising sequentially pressing then releasing the plunger rod is used. The second bulbous section on the stem is sized and shaped to perform a function of a sliding, blocking element of a check valve, restricting flow back into the rear chamber and causing the plunger valve to be forced proximally to relieve pressure build-up in the front chamber. In this manner, contents of the rear chamber are "pumped" into the front chamber for mixing. Once mixing is complete, the cap is removed for further use and delivery of the resulting mixture.

Second and third simple mixing syringe embodiments each comprise a novel pressure-actuated valve and a separate check valve. The pressure actuated valve comprises a pair of plungers and a stem comprising a bulbous section which closes a pathway in the most distal plunger. Applying sufficient pressure for a long enough period of time upon the plunger rod displaces the most distal plunger from the bulbous section of the stem and the more proximal plunger to open a chamber communicating pathway. The check valve is disposed to permit pumping of liquid from the rear chamber into the front chamber for mixing in a manner similar to the pumping procedure of the first mixing syringe embodiment.

Valve actuation of the second embodiment, like the first embodiment, requires applying force upon the plunger rod to create sufficient pressure within the barrel to open the pressure actuated valve. The piston valve maintains contents of the chambers disparate until an assertive, predetermined act upon the syringe plunger rod produces a sufficiently high pressure within the barrel for a long enough period of time to actuate the pressure-actuated valve to an open state. Once open, the check valve operates to permit diluent transfer into the mixing chamber in any syringe orientation as disclosed in Thorne '354. Once mixing is complete, gas can be purged from the front chamber using conventional syringe handling technique, before delivering the dose.

Of critical importance is presence of an elastic fluid within the mixing or more distal chamber wherein energy, resulting from pressure derived from positive force applied upon the plunger rod of the syringe, can be stored. In a preferred embodiment, at least a portion of the stored energy effects displacement of the valved piston in a direction opposite the applied force once that force is terminated, thereby changing size of the mixing chamber relative to the diluent chamber and providing opportunity for additional dispensing of fluid through the plunger valve by subsequent application of compressive force against the plunger rod. In this manner, by repeated application of force on the plunger rod, content of the diluent chamber is displaced ("pumped") into the chamber where mixing occurs.

A more detailed disclosure for the pressure-actuated valve is provided for clarification as follows:

The pressure-actuated valve comprises a valved piston and a mooring piston and an elongated displaceable stem. The valved piston and mooring piston are joined together by the stem which is medially disposed through holes in both pistons. The stem comprises a distally disposed bulbous section and more proximally disposed footings. When disposed within a through hole in the valved piston, the bulbous section occludes the hole in the distal piston to fluid flow and provides a releasable latch within the valved piston.

The footings are anchored to the proximal end of the mooring piston to provide a closed valve assembly. The mooring piston has an open medially disposed fluid pathway whereby upstream pressure is communicated to the valved piston. Applying pressure via the plunger rod produces pressure differential across the combination which forces the valved piston distally relative to the mooring piston to unlatch and thereby extract the bulbous portion from the through hole, opening the piston valve. As the valve piston is displaced from the mooring piston upon opening, a visual indicator is provided as evidence for valve opening.

Mixing Syringes with Flush

In a mixing syringe with flush embodiment, another valve which is actuated by sensing the end of a dose dispensing cycle (i.e. after completely emptying a dose from the mixing chamber) is used to initiate fluid communication from a flush containing chamber. In this manner, a dose bolus is fully dispensed before flushing. For this purpose, the other valve is actuated at a time which permits substantially continuous flow from the syringe (i.e. liquid from the flush chamber is then dispensed). As an example, such flushing can be used to clear communicating lines of drug between the syringe and a treated patient.

An additional chamber for flush fluid is provided within the barrel by a flush valve assembly. Actuation of the flush valve assembly should occur at the end of a front or dose chamber dispensing cycle.

In a preferred mixing syringe with flush embodiment, a direct communication, which occurs when a most distal syringe reaches the distal end of an associated syringe, communicates actuation conditions to an upstream stem valve. In such a case, an elongated stem associated with the pressure-actuated mixing valve is displaced within an associated piston as a sensor for valve travel as a dose dispensing is completed. Upon contact with the distal syringe inner surface, the stem is stopped. A bulbous section on the stem is sized and disposed to occlude flow though the mixing valve until the dose bolus is to be dispensed. At this time, the occluding part is displaced from the associated piston to open a pathway through the mixing valve and, simultaneously, forced distal displacement of the flush containment piston valve provides for communication with a second stem of the flush piston valve thereby subsequently opening the flush valve. In all cases, a clear fluid pathway is provided for flushing fluid flow upon opening of the flush piston valve.

Given a device comprising the parts disclosed above for a mixing syringe, operation is as follows:

with the cap disposed to close the distal end of the barrel of the associated syringe, apply sufficient compressive force against the plunger rod for a long enough period of time to open the mixing valve;

apply intermittent force against the plunger rod to dispense liquid from the proximal chamber into the distal chamber for mixing;

allow sufficient time for mixing;

remove the cap;

purge gas from the syringe; and dispense the mixed dose.

If the mixing syringe is self-contained and has a second valve combination for an added flush, continue with the following steps:

once the dose bolus is dispensed, continue displacement of the plunger rod to dispense flush through a valve opened by sensing completion of the mixed dose dispensing cycle; and continue displacement of the dose until a stop disposed between the syringe and plunger rod curtails plunger rod distal motion (such a stop is used to eliminate unwanted reflux flow).

It should be noted that a gas filter associated with the flush valve obviates gas (air) flow from the flush chamber. It should also be noted that this embodiment has a preference because all components are contained within a single syringe.

However, as noted above, up to four pistons and three valves are required for the above disclosed embodiment of a mixing syringe with flush. As use of four pistons and three valves results in potential for higher cost and complexity than may be desired, another embodiment which utilizes a separate diluent source vessel (which may be a second syringe) and a dual chamber syringe provides an embodiment which, under most mixing applications, is preferred over the more complex system disclosed supra. In this other embodiment, a dual chamber syringe which is fully disclosed in U.S. patent application Ser. No. 14/921,343

(Thorne '343), from which this U.S. Patent Application continues, is used as a mixing syringe. In such a case, a diluent is provided by the separate vessel rather than being disposed within a chamber of the mixing syringe, itself. Note that use of a separate vessel assures isolation between dose and diluent until mixing is commenced without concern for communicating valve integrity.

The separate vessel is provided with a compatible communicating fitting (e.g. a female luer fitting) for directly connecting and dispensing diluent (mixing liquid) into a mixing chamber of the dual chamber syringe. A traditional pre-filled syringe may be used as such a vessel, but such requires an additional female/female fitting. Commonly, as disclosed supra, a dose material (which may be a lyophilized solid) is initially disposed in the mixing chamber. To initiate mixing, the separate vessel is affixed to the mixing syringe, via the male mixing syringe luer fitting, and diluent is transferred into the mixing chamber. Gas and excess dose can be purged from the mixing chamber into the separate vessel while the separate vessel remains affixed thereto. Once mixing and purging is complete and the separate vessel is uncoupled from the mixing syringe, dose delivery followed by a flush from the rear chamber is accomplished as fully disclosed in Thorne '343).

Valve Pistons

There are a number of items which must be considered in the design of a dual chamber syringe piston valve which is displaced by force of a differential fluid pressure, rather than by a plunger rod, with primary goal of keeping material on each side of the valve disparate. One compounding item is compressive set of some butyl rubber and other piston making materials. A compressive set reduces the dynamic effect expected of incompressible material being forced a against a solid wall (e.g. an inner syringe barrel wall) such that any displacement from that wall results in momentary piston-to-wall separation.

Generally, a lubricant, such as silicone is applied to communicating surfaces within a syringe barrel to facilitate piston displacement. Commonly, the lubrication effect is diminished by such events as disuse and long-standing syringes exhibit need for significant force upon the syringe plunger rod to initiate displacement, referenced herein as "stiction".

One of the problems associated with stiction in multi-chamber syringes is that stiction does not occur uniformly about a piston and, often, fluid driven displacement can be preceded by sufficient piston distortion to permit blow-by. Such distortion can lead to piston ring to syringe barrel inner wall separation and significant blow-by of liquid, a condition which is highly undesirable.

Another source of piston distortion is the result of a pressure differential along the longitudinal axis of the piston. A pressure differential which is greater proximally can cause the distal face of the piston to bulge or balloon. As stated supra, pressure differential along with stiction of sufficient force may cause sufficient bulging piston distortion to result in blow-by.

To allay one cause of blow-by resulting from pressure applied piston distortion, a circumferential barrier can be molded about the proximal end of a piston made according to the instant invention. The barrier is close fitting about the inner surface of the barrel and has an elongated structure which is so affixed to the proximal end of the piston that canting associated with stiction displaces the barrier against the syringe inner wall forming a seal against an area where ring to wall separation occurs, thereby obviating blow-by.

To ameliorate consequences of canting and pressure provoked bulging, a seal/support structure can be used. This structure comprises a tight fitting ring of sufficient length to be inserted into a cavity in the valve piston for deterring piston canting. In addition the structure comprises a distally disposed shield which obstructs effective application of fluid pressure against the distal portion of the valve piston thereby reducing effect of bulging or ballooning.

Measured dimension change in pistons after being disposed within a syringe barrel showed a decrease in ring diameter in the range of 2½% in some piston materials used. In such applications, ring diameters should be appropriately enlarged.

Another counter to piston ring to syringe wall separation, caused by stiction, fluid pressure and subsequent piston deformation can be provided by structure of piston fluid interfacing structure. Generally, piston material is sufficiently compliant that applying a pressure differential across such a piston results in some piston deformation. As stated supra, such deformation can result in opening an undesired pathway for blow-by.

However, interfacing structure of the piston can be fashioned to oppose blow-by conditions. By providing a convex shape to each fluid interfacing surface and a directly communicating coupling from that interfacing surface to valve piston rings, pressure caused piston deformation can be directed radially to provide resultant pressure and force through the rings to augment ring-to-barrel wall seal. For this reason, a pre-filled dual chamber syringe piston, stored long enough to experience stiction, can be displaced without incurring blow-by.

Accordingly, it is a primary object to provide a mixing syringe which is disposed in a conventional commercial syringe barrel.

It is another primary object to provide a mixing syringe with flush which is disposed in a conventional commercial syringe barrel.

It is yet another primary object to provide a mixing syringe in which two disparate chambers are separated by a pressure-actuated piston valve, said valve being actuated to an open state by application of a predetermined force for a period of time.

It is still another primary object to provide a mixing syringe system which comprises a dual chamber syringe and a separate pre-filled vessel with a fitting compatible with the dual chamber syringe such that the mixing chamber is in the distal or first dispensed chamber of the dual chamber syringe and the proximal or following dispensing chamber provides a flushing solution.

It is a fundamental object to provide a mixing syringe with a conventional syringe barrel with a flush wherein a flush cycle occurs only after complete dispensing of a mixed dose.

It is an important object to provide a mixing syringe with flush which provides a stop at the end of a flush cycle to thereby obviate end-of-dispensing reflux flow.

It is a very important object to provide a mixing syringe assembly and multi-chamber syringe combination having three disparate chambers whereby all mixing and flushing components are disposed within a single syringe.

It is an object to provide a mixing syringe assembly which has a chamber, which ultimately contains a mixed solution, which can be purged of air prior to medication delivery.

It is another very important object to provide a barrier providing secondary seal which guards against blow-by caused by stiction or piston deformation.

It is yet another very important object to provide a seal/support which deters both canting and ballooning.

It an extremely important object to provide a valve piston, having opposing fluid facing surfaces which when deformed by a positive pressure differential are capable of communicating positive force to associated rings to obviate blow-by.

These and other objects and features of the present invention will be apparent from the detailed description taken with reference to accompanying drawings.

BRIEF DESCRIPTION OF THE DRAWINGS

FIG. 1 is a side elevation of a conventional medical syringe.

FIG. 2 is a side elevation of a stem of a piston valve made according to the instant invention.

FIG. 3 is a cross section of a valve piston made according to the instant invention.

FIG. 8 is a schematic representation of the assembly seen in FIG. 7 with the plunger rod, associated piston and valve further displaced into the barrel until the stem collides with the distal end of the barrel.

FIG. 9 is a schematic representation of the assembly seen in FIG. 8 wherein the stem is displaced to change the valve to an open state of a check valve and thereby permit fluid disposed in a chamber between the two pistons to be displaced into the chamber containing the lyophilized material.

FIG. 9A is a side elevation of the piston valve (seen in FIGS. 9 and 3A) closed as a check valve to proximal fluid flow.

FIG. 9B is a side elevation of the piston valve seen in FIG. 9A open to distally directed flow.

FIG. 10 is a schematic representation of the assembly seen in FIG. 9 with the piston valve displaced proximally into contact with the plunger rod piston.

FIG. 13 is a schematic representation of an assembly of a second mixing syringe embodiment made according to the present invention with some parts shown in cross-section.

FIGS. 14-16 illustrate pressure-actuated valve components of the second mixing syringe as follows:

FIG. 14 is a cross-section of a valve piston which is a part of the second mixing syringe seen in FIG. 13.

FIG. 15 is a cross-section of a mooring piston which is also a part of the second mixing syringe seen in FIG. 13.

FIG. 16 is a side elevation of a valve stem, also a part of the second mixing syringe seen in FIG. 13.

FIG. 17 is a schematic representation of the assembly seen in FIG. 13 wherein a pressure-actuated valve is open as a result of force applied to a plunger rod.

FIG. 18 is a schematic representation of the assembly seen in FIG. 17 after displacing diluent (liquid) from a proximal or rear chamber into a distal or front chamber for mixing.

FIG. 19 is a schematic representation of the assembly seen in FIG. 18 with a portion of the open valve displaced by force applied to the plunger rod to further dispense liquid into the front chamber from the open valve.

FIG. 20 is a schematic representation of the assembly seen in FIG. 19 vertically disposed for purging gas from the front chamber.

FIG. 21 is a schematic representation of the assembly seen in FIG. 20 after dispensing of liquid from the front chamber.

FIGS. 22-27 illustrate components of a third mixing syringe embodiment of the present invention comprising a pressure-actuated displacement valve as follows:

FIG. 22 is a cross-section of a conventional syringe barrel.

FIG. 23 is a side elevation of a cap for a luer fitting associated with the barrel seen in FIG. 22.

FIG. 24 is a side elevation of a conventional plunger rod and associated piston.

FIG. 25 is a cross-section of a valve piston which is a key part of a valve of the third mixing syringe.

FIG. 26 is a cross-section of a mooring piston which is another key part of a valve of the third mixing syringe.

FIG. 27 is a side elevation of a valve stem used in the third mixing syringe valve.

FIG. 27A is a schematic representation of an assembled pressure-actuated valve comprising parts seen in FIGS. 25-27.

FIG. 27B is a magnified schematic representation of the valve seen in FIG. 27A opened by applied pressure.

FIG. 27C is a magnified schematic representation of the valve seen in FIG. 27B closed to flow by displacement of the valve stem.

FIG. 34 is a side elevation of a cap for closing and sealing a luer fitting of a conventional medical syringe barrel, such as the barrel seen in FIG. 35.

FIG. 35 is a cross-section of a conventional syringe barrel similar to the barrel of FIG. 35 being elongated for housing flush valving components.

FIG. 36 is a side elevation of a conventional plunger rod with an integral stoop and associated piston, similar to the plunger rod and piston seen in FIG. 36.

FIG. 37 is a cross-section of a dual constriction hole piston which is a key part for a pressure-actuated valve according to the present invention for the second embodiment of a mixing syringe with flush.

FIG. 38 is a cross-section of a mooring piston for the pressure-actuated valve.

FIG. 39 is a side elevation for an elongated stem for the pressure-actuated valve.

FIG. 40 is a cross-section of a piston for the displacement valve with a gas filter part for keeping gas from being delivered from the most proximal chamber.

FIG. 41 is a side elevation of a stem associated with the piston seen in FIG. 40 used for the displacement valve.

FIG. 41A is a magnified schematic representation of an open valve, in a state similar to the pressure-actuated valve seen in FIG. 27B.

FIG. 41B is a magnified schematic representation of an open valve, in a state similar to the pressure-actuated valve seen in FIG. 27C.

FIG. 42 is a schematic representation of a mixing syringe with flush assembly, fashioned within the scope of the instant invention, with a complement of solid matter in a front chamber and liquid in two more proximal chambers, prepared for delivery as a self-contained mixing and flush syringe system.

FIG. 43 is a schematic representation of a mixing syringe with flush assembly similar to the assembly seen in FIG. 42, but with a pressure-actuated valve opened by force applied to the plunger rod.

FIG. 44 is a schematic representation of a mixing syringe with flush assembly wherein the valve, opened as seen in FIG. 43, has permitted displacement of liquid from a middle chamber into the distal or front chamber for mixing.

FIG. 45 is a schematic representation of a mixing syringe with flush assembly in a state following that seen in FIG. 44 wherein force upon the plunger rod upon emptying of the middle chamber closes a chamber formed by valve opening to evacuate fluid from the pressure-actuated valve to reduce dead space.

FIG. 46 is a schematic representation of a mixing syringe with flush assembly rotated from a position seen in FIG. 45 for purging gas from the distal or front chamber.

FIG. 50 is a schematic representation of a dual chamber syringe made according to the present invention to be used as part of a mixing syringe system.

FIG. 51 is a schematic representation of a pre-filled syringe having a female luer fitting for use in a system with the syringe seen in FIG. 50.

FIG. 52 is schematic representation of a pouch made of deformable material also having a female luer fitting fore use in a system with the syringe seen in FIG. 50.

FIG. 56 is a side elevation of a piston valve similar to the piston valve of the dual chamber syringe seen in FIG. 50.

FIG. 56A is a cross section of a piston valve similar to the piston valve seen in FIG. 56, but having a cavity, which permits added storage for gas, disposed about a tube which opens to a liquid only zone.

FIG. 57 is a side elevation of a valve piston which is similar to the piston valve seen in FIG. 56, but with a barrier part affixed to a proximal end.

FIG. 58 is a perspective providing a view of the distal end of the piston valve seen in FIG. 57.

FIG. 59 is a perspective of the providing a view of the proximal end of the piston valve seen in FIG. 58.

FIG. 60 is a side elevation of the piston valve seen in FIG. 56 disposed in a section of a syringe barrel.

FIG. 61 is a side elevation of the piston valve seen in FIG. 57 disposed in a section of a syringe barrel.

FIG. 64 is a cross section of a valve piston comprising oppositely disposed convex fluid interfacing surfaces which communicate with associated valve piston ring structure.

FIG. 65 is a cross section of a valve piston, similar to the valve piston seen in FIG. 65, but with one fluid interfacing surface disposed to provide a cavity which is increased in size for gas capture.

DETAILED DESCRIPTION OF THE ILLUSTRATED EMBODIMENTS

In this description, the term proximal is used to indicate that segment of a device which is a closest part to an object of reference (generally a device user). The term distal refers to an opposite orientation. Reference is now made to the embodiments illustrated in FIGS. 1-65 wherein like numerals are used to designate like parts throughout. Primes of numbers are generally used for parts which are similar in shape and/or function but not exactly the same as parts identified by the numbers themselves.

Mixing Syringe Embodiments

Figure 1:
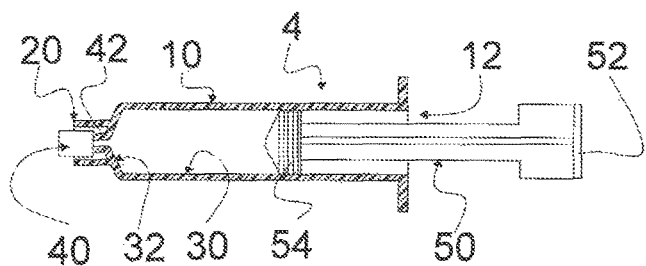
FIGS. 1-3 illustrate components of a first mixing syringe embodiment of the present invention comprising a pressure-actuated displacement valve as follows.

Reference is now made to FIGS. 1-12 wherein a first embodiment of an assembled mixing syringe (see, for examples, FIGS. 7-12) configured according to the instant invention is disclosed. A conventional medical syringe 4 comprising a barrel 10, used in the assembly of such a mixing syringe, is seen in FIG. 1. Barrel 10 comprises an open end 12 which is generally proximal to an attending technician or user and an opposite end which is closed about a luer lock fitting 20. Between end 12 and fitting 20, barrel 10 comprises an elongated inner cylindrical surface 30 of substantially constant diameter. Internally, surface 30 is blended and diminished about fitting 20 to form a distal or front inner surface 32. Such barrels are widely known and used commercially in medical practice.

A cap 40 is disposed about the luer portion of fitting 20 to close barrel 10 distally. A plunger rod and piston combination 50 is disposed to close access to open end 12. Generally, such combinations comprise two parts, a plunger rod 52 and a piston 54. As is well known in medical art, combination 50 is disposed in open end 12 of barrel 10 for purposes of displacing fluid therein.

Also, as well understood in medical art, piston 54 is cylindrical in shape and is sized and shaped to compressively seal against surface 30 to efficiently wipe against surface 30 to restrain fluid from proximal egress outside barrel 10 when displaced therein. To accomplish the seal and effective wiping, such pistons are generally oversized by a given margin (e.g. 4-6%) and made out of incompressible, but flexible material, thereby producing a significant pressure between syringe barrel and piston. It should be noted that such pressure is communicated medially inward in pistons. This communicated pressure is used effectively in piston parts of the instant invention as disclosed hereafter.

Figures 2, 3, 3A:
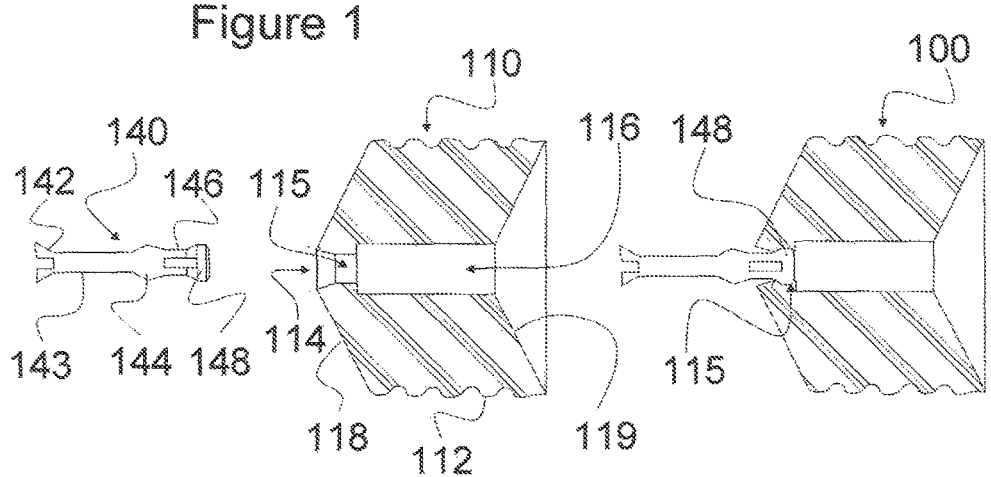
FIG. 3A is a cross section of a piston valve assembled from the stem seen in FIG. 2 and valve piston seen in FIG. 3.

Components of a displacement-actuated valve, generally numbered 100 hereafter, are found in FIGS. 2 and 3 but not seen as an assembled unit in figures cited supra. A valve piston 110 is seen in FIG. 3. Piston 110 comprises a cylindrical side surface 112 having cylindrical dimensions consistent with piston 54. Further, piston 110 comprises three interconnecting through holes, a distal hole 114, a medially disposed hole 115 and a proximal hole 116. Piston 110 has a frustoconically shaped front surface 118 which is sized and shaped to conform with front surface 32 of barrel 10 to minimize barrel 10 dead space. Rear or proximal surface 119 of piston 110 is preferably frustoconically shaped for reasons clearly disclosed hereafter.

Stem 140, seen in FIG. 2, basically consists of five sections, a forward or distal impact section 142, an elongated rod section 143, a first bulbous section 144, an elongated leg section 146 and, a proximally disposed second bulbous section 148.

Reference is now made to FIG. 3A wherein an assembled valve 100 is seen. Note that bulbous section 148 is sized and shaped to fixedly occlude hole 115 when disposed therein. When section 148 is so disposed, valve 100 is closed.

In a mixing syringe made according to the present invention, barrel 10 is divided into two chambers by deposition of valve 100 therein as part of an assembly process. As seen in FIG. 7A, a fully assembled deliverable mixing syringe device 150 comprises a valve 100 which divides barrel 10 into a distal chamber 152 and a proximal chamber 154. A lyophilized material 160 is disposed in chamber 152 and a diluent (mixing solution) 170 is disposed in chamber 154.

Figure 4:
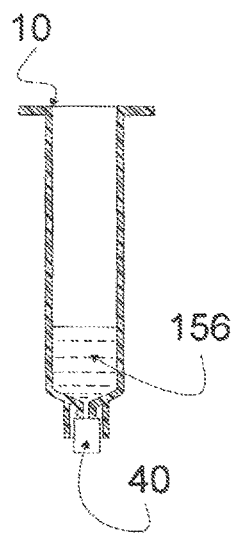
FIG. 4 is a cross section of a capped barrel of the medical syringe seen in FIG. 1 with a predetermined dose of medicine to be lyophilized within the barrel disposed therein.
Figure 5:
FIG. 5 is a cross section of the barrel seen in FIG. 4 with a lyophilized material (solid, likely powdered) disposed therein.

An exemplary method for assembling device 150 is provided by steps seen in FIGS. 4-7A. All of the following steps should be performed under sterile conditions. As seen in FIG. 4, a predetermined volume of liquid "dose" material 156 is displaced into a capped barrel 10. Liquid material 156 is freeze-dried (lyophilized) to a solid 160 as seen in FIG. 5.

Figure 6:
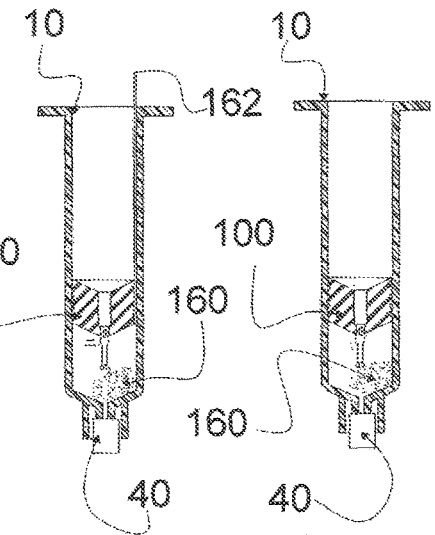
FIG. 6 is a cross section of the barrel and material seen in FIG. 5 with the piston valve seen in FIG. 3A displaced therein along a straw to permit gas escape during valve disposition, thereby providing a distal chamber for the lyophilized material.
Figure 6A:
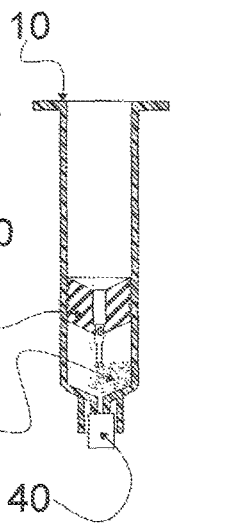
FIG. 6A is a cross section of the barrel, material and valve seen in FIG. 6 with the straw withdrawn.

Using a straw 162 (or rod) to permit trapped gas to escape, valve 100, in an initial closed state, is displaced into barrel 10, to provide a chamber 152 of predetermined volume, as seen in FIG. 6. Once valve 100 is so positioned, straw 162 is removed as seen in FIG. 6A.

Figure 7:
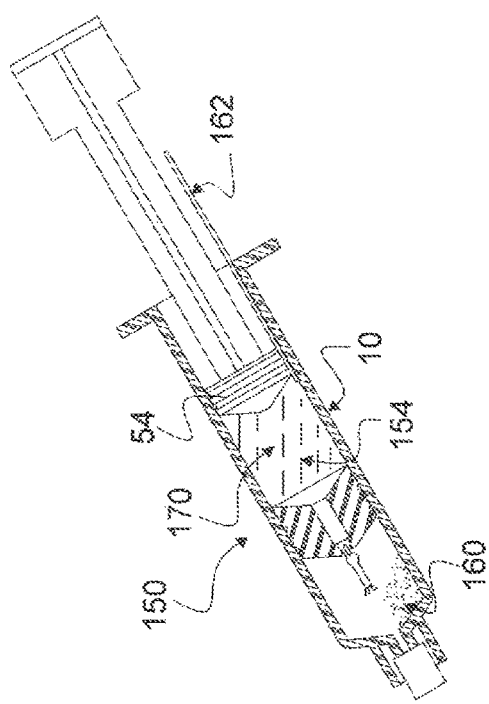
FIG. 7 is a schematic representation of a cross section of an assembly comprising the barrel, material and valve seen in FIG. 6A and a plunger rod and associated piston displaced into the barrel, to capture a bolus of liquid within the barrel in a proximal chamber, the plunger rod being displaced along another straw which permits gas escape while displacing the associated piston therein.
Figure 7A:
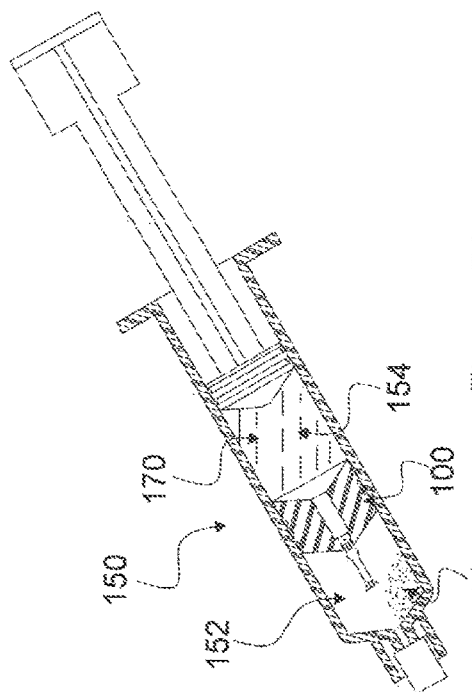
FIG. 7A is a schematic representation of the assembly seen in FIG. 7 with the other straw removed.
Figure 28:
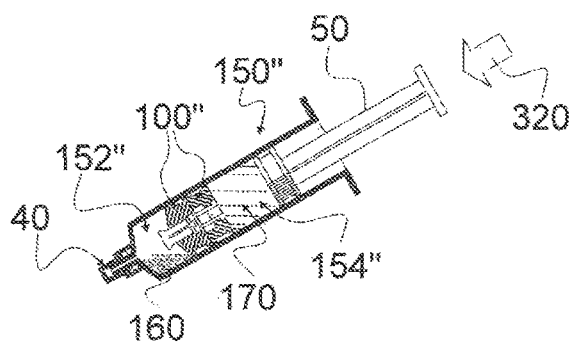
FIG. 28 is a schematic representation of an assembly of the third mixing syringe comprising parts seen in FIGS. 22-27, a solid material to be liquified in a front or distal chamber and diluent liquid in a rear or proximal chamber.

Then, a predetermined volume of liquid (diluent 170) is dispensed into barrel 10 followed by inserting piston 54 to form chamber 154 (see FIG. 7). Again, a straw 162 is used to permit excess gas to escape from barrel 10 during piston 54 insertion. With piston 54 in place and straw 162 removed, device 150 is completely assembled and ready for delivery to a mixing site (see FIG. 7A).

To mix liquid 170 with material 160, a pathway from chamber 154 to chamber 152 must be created. Such is accomplished by displacing valve 100 distally until section 142 impacts front surface 32 of syringe barrel 10 (see FIG. 8). After impact, continued displacement of valve 100 displaces section 148 from hole 115 removing the associated occlusion and opening a pathway 164 (see FIG. 9B) for displacement of diluent 170 into chamber 152.

The method for displacing liquid from chamber 154 into chamber 152 not only requires opening valve 100, but also providing an effective check valve which is permissive to liquid flowing from chamber 154 into chamber 152, but also which obstructs liquid from returning to chamber 154, once displaced.

Check valve operation is demonstrated in FIGS. 9A and 9B. Note in FIGS. 9A and 9B section 148 is displaced from hole 115 to open pathway 164. When distal pressure (noted by arrow 172) is greater than proximal pressure (noted by arrow 174 in FIG. 9B), section 144 of stem 140 is forced against a distal ring 176 created by distally diminishing the diameter of hole 115 relative to hole 114 (see FIG. 3) thus closing valve 100. As seen in FIG. 9B, when proximal pressure (indicated by arrow 174) is greater than distal pressure (arrow 172, FIG. 9A) section 144 of stem 140 is displaced away from ring 176. These two conditions for displacing section 144 provides for a pumping action which displaces fluid from chamber 154 into chamber 152 when plunger rod 50 is sequentially displaced into barrel 10.

With pressure increased in chamber 152 to force section 148 from hole 115, as seen in FIG. 8, and pressure indicated by arrow 172 greater than pressure proximally disposed relative to valve 100, valve 100 is first opened by displacement of section 148 and closed by impact of section 144 against ring 176 (see FIG. 9A). Equalization of forces due to increased pressure in Chamber 152 displaces valve 100, chamber 154 and plunger rod 50 proximally, as seen in FIG. 9. Sequentially "pumping" plunger rod 50 (see arrow 178) into barrel 10 then displaces diluent 170 into chamber 152 to form mixture 180 as seen in FIG. 10.

Figure 11:
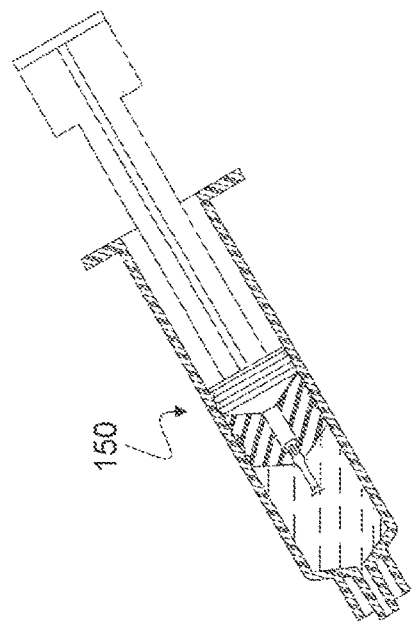
FIG. 11 is a schematic representation of the assembly seen in FIG. 10 with fluid from the proximal chamber displaced into the distal chamber to mix with material therein.
Figure 12:
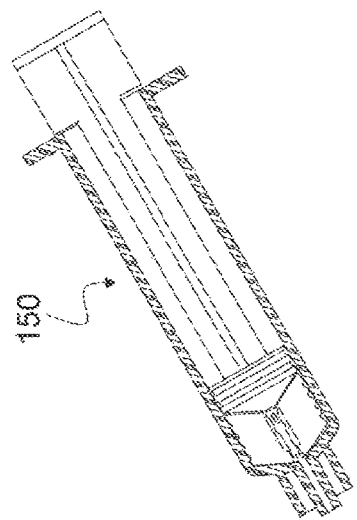
FIG. 12 is a schematic representation of the assembly seen in FIG. 11 with the mixture dispensed.

Once mixture 180 is appropriately mixed and/or incubated, cap 40 is removed and device 150 is prepared for dose delivery (by conventional syringe handling techniques which are well known in medical syringe dose delivery art) as seen in FIG. 11. Device 150 is seen emptied with dose fully delivered in FIG. 12.

A second embodiment of a mixing syringe is seen in FIGS. 13-20. A deliverable, pre-filled mixing syringe 150' is seen in FIG. 13. Device 150' comprises liquid 170 in a proximal chamber 154' and a solid (likely lyophilized) material 160 in a distal chamber 152' and a cap 40 which retains material therein. Chambers 152' and 154' are kept disparate by a closed pressure-actuated valve 100'.

Pressure-actuated valve 100' is comprised of three parts, a distal valve piston 110', an anchor piston 120' and a valve stem 140', as seen in FIGS. 14-16. Valve piston 110' comprises a distally disposed slit valve 200 which when closed provides an obstructing end of a medially disposed cylindrical hole 210 which is distally closed by valve 200. Further piston 110' comprises a cylindrical exterior side face 212 which is sized and shaped to act as a fluid displacing piston in a barrel 10 (seen in FIG. 13).

Anchor piston 120', seen in FIG. 15, comprises a relatively large receiving, distally disposed hole 220, sized and shaped to receive a bulbous portion of stem 140' while permitting flow to pass thereby. A second, more proximal hole 222 provides a diminished clearance and side support for an anchoring ring 224. Further, piston 120' has a cylindrical side surface 226 which is similar in size and function to the exterior side face 212 of piston 110'.

Valve stem 140', seen in FIG. 16, comprises a cylindrically shaped distal section 230 with a gap 232 which is sufficiently wide to permit adequate flow from more proximal chambers. Proximally disposed relative to section 230 is a bulbous part 240 which continues gap 232 approximately half way through part 240, the remaining portion 242 being sufficiently wide to block fluid flow when disposed within hole 210, as seen in FIG. 13. Extending proximally from portion 214 is an anchoring portion 250 comprising elongated leg parts, commonly numbered 252 and anchoring, radially extended feet, commonly numbered 254. Feet 254 are sized and shaped to be firmly caught and affixed within anchoring ring 224, see FIG. 15.

By applying force in direction of arrow 260 (seen in FIG. 17) to piston and plunger rod assembly 50, piston 110' is displaced proximally relative to piston 120' displacing bulbous part 240 from hole 210. This action opens valve 100' to distally directed fluid flow.

Further repeatably applied force upon assembly 50 in direction of arrow 260 (seen in FIG. 18) "pumps" fluid initially disposed in chamber 154' (see FIG. 17) into chamber 152' (see FIG. 18). Also force applied in direction of arrow 260 can cause pistons 110', 120' and 54 to be fully compressed into one another, as seen in FIG. 19. Once, so compressed, device 150' can be vertically oriented with cap 40 removed, as seen in FIG. 20, to be purged of gas by conventional syringe purging technique (by applying force in direction of arrow 260'). A fully emptied device 150' is seen in FIG. 21.

A third embodiment of a mixing syringe 150" made according to the instant invention is seen in various parts and forms in FIGS. 23-33. Mixing syringe 150" comprises a cap 40 (seen in FIG. 23), a syringe barrel 10 (seen in FIG. 22), a plunger rod and piston assembly 50 (seen in FIG. 24), a valve piston 110" (seen in FIG. 25), an anchor piston 120" (seen in FIG. 26) and a valve stem 140" (seen in FIG. 27).

Valve piston 110" has a through medically disposed hole 300 which comprises a frustoconically shaped distal opening 302 which communicates with an elongated, proximal cylindrical hole 304. Similar to valve piston 110', piston 110" comprises an exterior side surface 308 which is sized and shaped to wipe cleanly along the inner surface 30 of barrel 10. Also piston 110" has a distal front surface which conforms in size and shape to distal inner surface 32 of barrel 10.

Anchor piston 120" (seen in FIG. 26) is similar in size, shape and function to piston 120 seen in FIG. 5. A through hole 130 is disposed through piston 120" for anchoring and distal communication of stem 140".

Valve stem 140" is similar, proximally, to stem 140 seen in FIG. 6, having proximally disposed legs 146 and anchoring feet 148. A medially disposed bulbous section 144" is similar to bulbous section 144. However, distal from bulbous section 144", stem 140" comprises an elongated cylindrical section 142" which communicates distally with a frustoconically shaped plug part 310. Plug 310 has a frustoconically shaped proximal section 312 which, when nested tightly in opening 302, see FIG. 25, plugs hole 300, thus, when so inserted, stem 140 and piston 110" comprise an effective one-way slider valve.

An assembled pressure-actuated valve 100" is seen in FIG. 27A. Being compliant, though made from incompressible material, pistons 110" and 120" readily accept displacement of stem 140" through holes 300 and 130. Note that, when so assembled, bulbous section 144" closes valve 100" and feet 148 are anchored.

As seen in FIG. 27B, application of fluid force (pressure differential) in direction of arrow 316 by applying force to a plunger rod assembly (such as assembly 50) when valve 100" is disposed in a syringe barrel (such as barrel 10), displaces piston 110" distally (in direction of arrow 316). Such displacement occurs when sufficient pressure is communicated through piston 120" against a proximal face 320 of piston 110". For this reason, it is recommended that a communicating space (not shown in FIG. 27A) be available for communicating the force of pressure against face 320. It should be noted that differential pressure against face 320 relative to total pressure against valve 100" must be sufficient to displace piston 110" rather than valve 100" to actuate valve 100" to an open state.

Once valve 100" is opened, as seen in FIG. 27B, liquid flows from a more proximal chamber (e.g. chamber 154' into chamber 152' (see FIGS. 17 and 18) until pressures in the two chambers are equilibrated. At such time, removal of force from the forcing plunger rod reverses the pressure differential as indicated by arrow 318 in FIG. 27C. This reversed pressure differential causes action of a slider valve displacing plug 310 section 312 of stem 140" into a plugging state in opening 302, as seen in FIG. 27C. Repetitive application of force thereafter can be used to displace fluid from the more proximal chamber into the distal chamber of the syringe for mixing.

Figure 29:
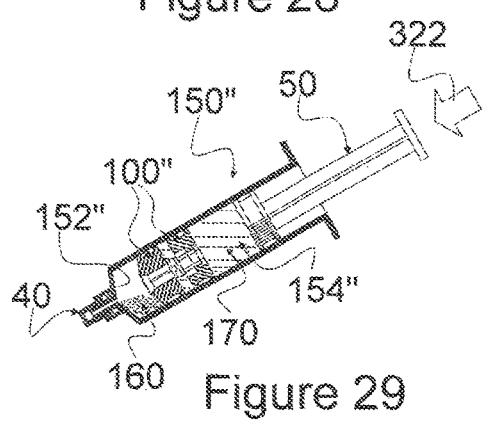
FIG. 29 is a schematic representation of the assembly seen in FIG. 28 wherein force applied to the plunger rod has produced pressure inside the syringe barrel and opened the third mixing syringe valve.

FIGS. 28-33 illustrate steps associated with use of a pre-filled mixing syringe 150" delivered with diluent 170 resident in a proximal chamber 154" and, in this case, a solid material dose 160 disposed in a distal or front chamber 152". As disclosed supra, application of force on plunger assembly 50 in direction of arrow 320, opens valve 100". Once valve 100" is opened, as seen in FIG. 29, repetitive application of force on plunger assembly 50 in direction of arrow 322, displaces diluent 170 into chamber 152" for mixing with dose material 160.

Figure 31:
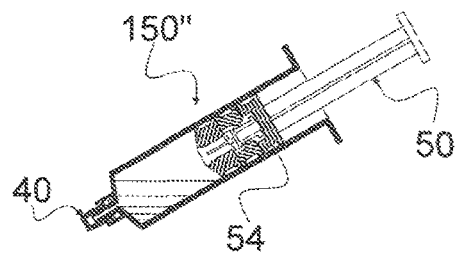
FIG. 31 is a schematic representation of the assembly seen in FIG. 30 wherein force applied to the plunger rod has displaced a portion of the valve distally, forcing diluent from the valve and reducing valve dead apace.
Figure 30:
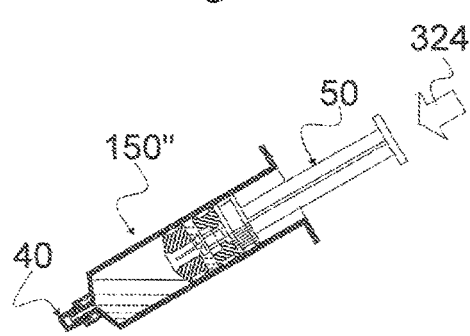
FIG. 30 is a schematic representation of the assembly seen in FIG. 29 wherein diluent is displaced from the rear or proximal chamber into the front chamber.

Once plunger rod piston is in contact with anchoring piston 120" (as seen in FIG. 30), further application of force in direction of arrow 324 can force pistons 110" and 120" together as seen in FIG. 31, thereby reducing total diluent dead space. For such to occur, piston must have a distal cavity (not shown) sufficient large to receive feet 148 of stem 140".

Figure 32:
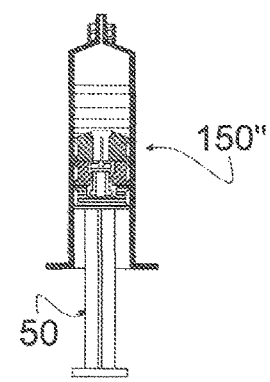
FIG. 32 is a schematic representation of the assembly seen in FIG. 31 rotated for purging gas from the front or distal chamber.
Figure 33:
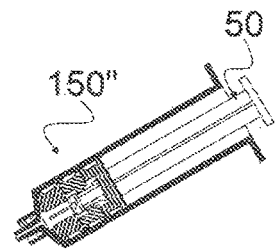
FIG. 33 is a schematic representation of the assembly seen in FIG. 32 with the front chamber emptied.

Purging of gas from syringe 150" is accomplished by removing cap 40, orienting syringe 150" vertically, as seen in FIG. 32, and following conventional syringe gas purging technique. An emptied syringe 150" is seen in FIG. 33.

Mixing Syringes with Flush Embodiments

Figures 34, 35, 36:
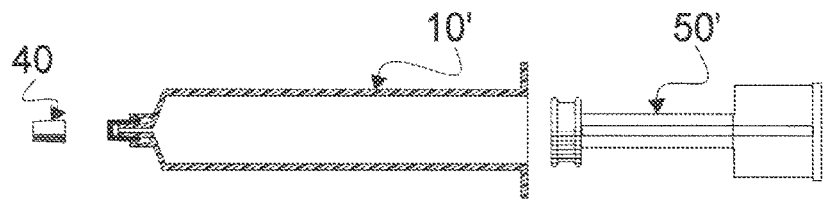
FIGS. 34-41 illustrate components of a second mixing syringe with flush embodiment of the present invention comprising a pressure-actuated displacement valve and a displacement valve as follows.

Attention is now drawn to FIGS. 17-33 wherein various parts and operational states of a first embodiment of a mixing syringe with flush 400 (syringe 400) are illustrated. As seen in FIGS. 42-49, syringe 400 (not seen as an assembled unit in FIGS. 24-41) comprises a cap 40 (FIG. 34), an elongated barrel 10' (FIG. 35), a plunger rod with a stop and piston assembly 50' (FIG. 36), a valve piston 410 (FIG. 37), an anchor piston 420 (FIG. 38), a valve stem 430 (FIG. 39), a dome valve insert 440 (FIG. 40) and a dome valve containment piston 450 (FIG. 41).

Cap 40 is used for capping and sealing a male luer fitting as disclosed supra. Barrel 10' is elongated (relative to barrel 10, disclosed supra) for providing space for three chambers and three separate pistons. Assembly 50' is similar in shape and function to assembly 50 (disclosed supra), but varied in length dimensions to accommodate an increased number of chambers and pistons.

Each of the pistons (410, 420 and 450) are sized and shaped to be displaced within barrel 10' and to keep associated proximal and distal chambers disparate. Piston 410 comprises a medially disposed hole 452 which is open on a proximal end and closed on a distal end by a slit valve 454. Valve 454 is similar in shape and function to a duck bill valve which would readily pass fluids distally, but obstruct flow directed proximally.

Piston 420 comprises a through hole 456 sized and shaped for fluid passage and for slidably guiding stem 430 through a portion thereof. Piston 420 also comprises an anchoring ring 458, the purpose for which is disclosed in detail hereafter.

Figure 39:
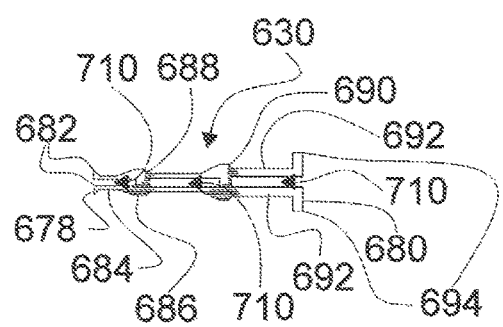
Figures 40, 41:
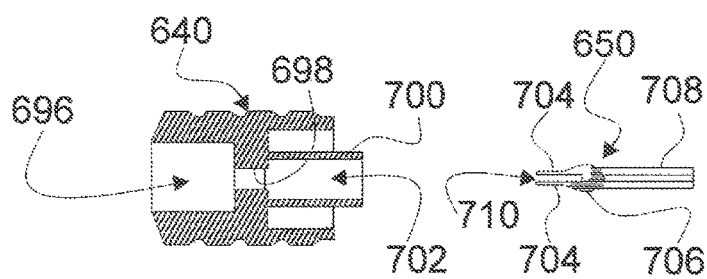

Stem 430, as seen in FIG. 39, comprises a bulbous section 460 which is sized and shaped to occlude fluid flow when disposed in hole 452. Distal from section 460, stem 430 comprises a duct 462 which is conducive to fluid flow when section 460 is displaced from hole 452. In addition, stem 430 comprises a pair of elongated legs, commonly numbered 464, which terminate in a pair of angled feet, commonly numbered 466. It may be noted that all distal and proximal faces interface with the same frustoconical dimensions. These angled interfaces provide a geometry which is conducive to gas flow from the interior of barrel 10' as is disclosed hereafter.

Valve insert 440 has a medially disposed dome shaped part 470 comprising a slit 472. As disclosed supra for valve 454, such a valve, when unencumbered about the dome, is permissive to flow directed toward the underside 472 of the dome while obstructive to flow directed toward the outside 474 of the dome. However, such is not the case for the valve function of valve insert 440. For attachment purposes, insert 440 has an attachment ring 476 disposed about dome shaped part 470.

As seen in FIG. 41, piston 450 has a cavity 480 which is sized and shaped to hold part 470 and slit 472 closed when disposed therein. A disk shaped groove 475 is disposed to provide rigid containment of attachment ring 476 and therefore dome part 470 within cavity 480 such that slit 472 is unable to open as long as the associated dome is fully resident within cavity 480. Further, piston 450 comprises a tube 482 which encloses a pathway 484 from a more proximal site in a liquid only zone of a chamber proximally associated with piston 450 to a dome part 470 valve closure.

Thus, opening of valve insert 440 is dependent upon forces which are sufficient to invert dome part 470. Such is the case when pressure against the exterior or convex surface of a dome is significantly greater than pressure on the interior or concave surface. However, when a piston in a syringe is displaced by such pressure differentials, the piston generally moves adjusting the pressure differential without dome inversion, until the piston is retarded from moving, at which time the dome inverts to actuate the associated valve to an open state. An inverted dome part 470 in such a state is seen in FIG. 42.

An assembled mixing syringe with flush 400 is seen in FIG. 43. An assembled closed valve 490 comprising piston 410, piston 420 and stem 430 divides barrel 10' into two chambers, 492 and 494. Chamber 492 containing a diluent 496 and chamber 494 containing gas and dose material 498. An assembled dome valve 500 comprising piston 450 and dome shaped part 470, further divides barrel 10' into a third chamber 510 which is mostly filled with a liquid flush 512. Plunger rod and piston assembly 50' close the third chamber proximally.

As seen in FIG. 44, applying force in direction of arrow 514, displaces piston 410 distally, freeing bulbous section 460 from hole 452 to open valve 400. Further application of force upon assembly 50' in direction of arrow 514' displaces diluent 496 to provide a mixture 520 of diluent 496 and material 498 in chamber 494. Once piston 450 is displaced into contact with piston 420, continued application of force against assembly 50' in direction of arrow 514" further opens valve 490 by displacing piston 420 toward piston 410.

Figure 47:
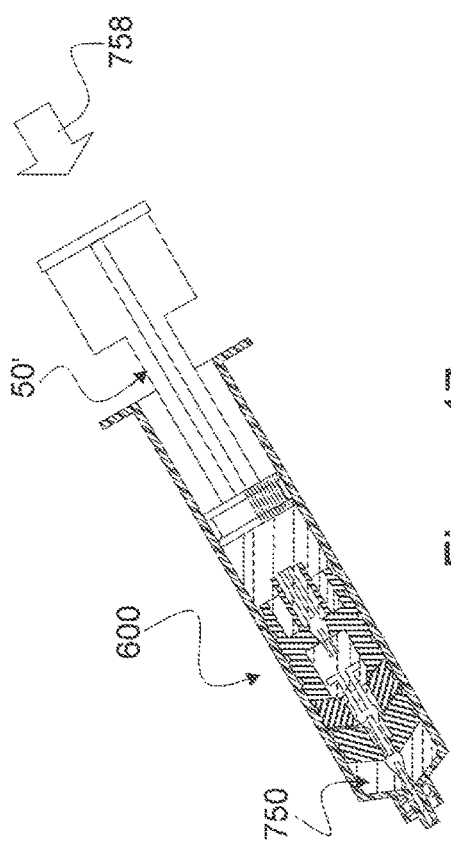
FIG. 47 is a schematic representation of a mixing syringe with flush assembly rotated from the state seen in FIG. 46 for dose delivery.

As illustrated in FIG. 47, with mixing complete, syringe 400 is oriented vertically with cap 40 removed for purging gas 530 from chamber 494 by application of force upon assembly 50' in direction of arrow 532.

Figure 49:
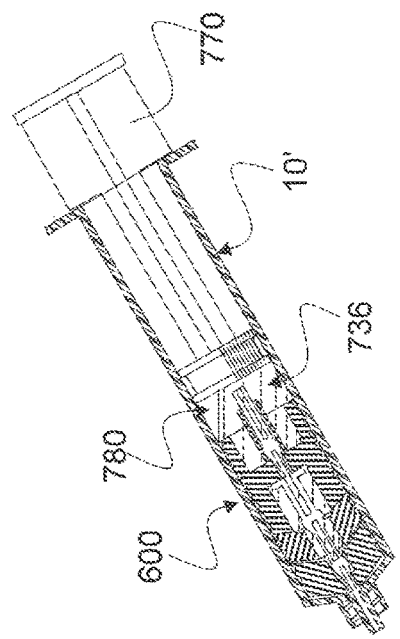
FIG. 49 is a schematic representation of a mixing syringe with flush assembly similar to that seen in FIG. 48, but with both dose and flush delivered (and gas in rear chamber trapped and undelivered).
Figure 48:
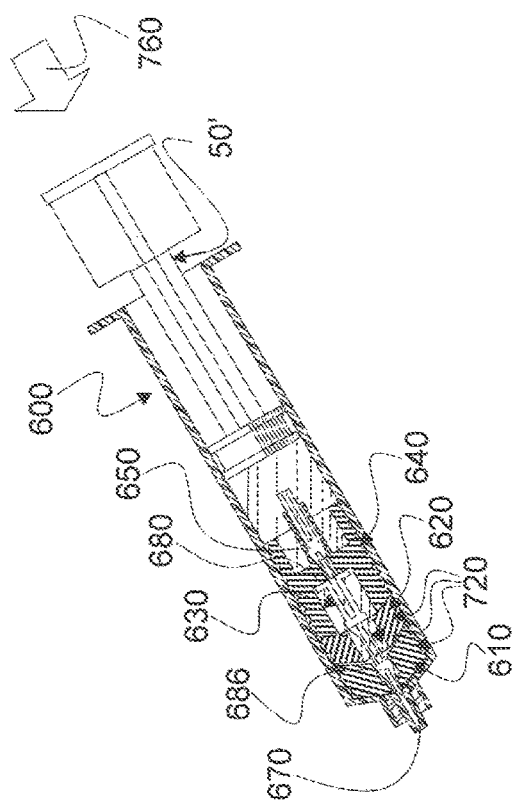
FIG. 48 is a schematic representation of a mixing syringe with flush assembly shows an assembly state following dose delivery as depicted in FIG. 47 wherein the dose fully delivered and the displacement valve is actuated for flush delivery.
Figure 50:
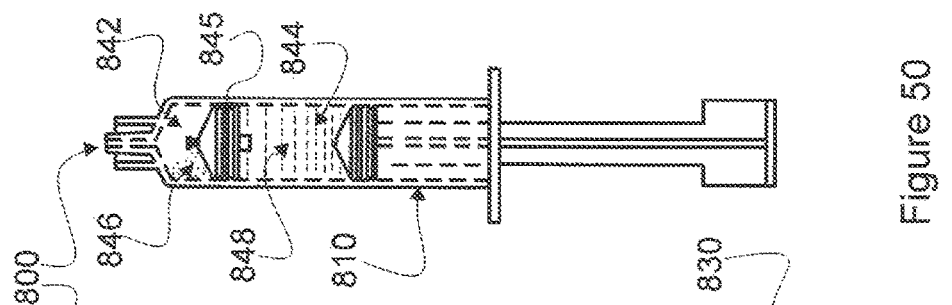
FIGS. 50-52 illustrate components of a third mixing syringe with flush embodiment of the present invention comprising a system employing a dual chamber syringe as follows.

Once chamber 494 is emptied, as seen in FIG. 48, further application of force upon assembly 50' when plungers 410, 420 and 450 are no longer free to move, applies sufficient pressure to invert dome shaped part 470. Inversion of part 470 opens pathway 484 for delivery of flush 512 from chamber 510, as seen in FIG. 49. A fully emptied syringe 400 is seen in FIG. 50. Note that wings 534 on plunger rod 52' provide a stop which assures liquid remains in the liquid only zone and reflux flow is obviated at the end of a dispensing cycle.

Reference is now made to FIGS. 34-49 wherein parts and methods of use of a second embodiment of a mixing and flushing syringe 600 are illustrated. Syringe 600 (not shown assembled in FIGS. 34-41) comprises a luer cap 40 (see FIG. 34), an elongated barrel 10' (see FIG. 35), a plunger rod with stop assembly 50' (see FIG. 36), a valve piston 610 (see FIG. 37), an anchor piston 620 (see FIG. 38), an elongated stem 630 (see FIG. 39), a flush release valve piston 640 (see FIG. 40) and a flush valve stem 650 (see FIG. 41). All pistons should be sized and shaped to segment barrel 10' having cylindrical side dimensions designed which wipe along barrel 10' surface 30, when displaced therein, and inhibit fluid communication along the inner surface 30. In addition, all interfacing parts should have complimentary geometries to reduce dead space in syringe 600.

Valve piston 610 comprises a frustoconically shaped distal and proximal faces, numbered 652 and 654, respectively. Distal face 652 should comprise complementary geometry for interfacing with barrel 10' distal interior face 32. Valve piston 610 also comprises a through hole 656 which opens proximally via large diameter segment 658 with a smaller diameter segment 670 distally engaged therewith and a distal frustoconically shaped distal opening 672.

Figures 37, 38:
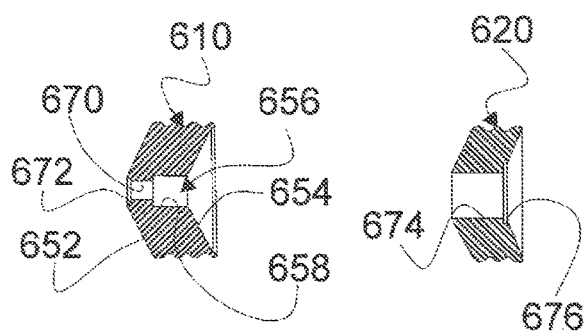

Anchor piston 620, as seen in FIG. 38, comprises a through hole 674 which is larger in diameter than segment 658. Proximal to hole 674, piston 620 comprises an inset groove 676, which acts as an anchor as disclosed hereafter.

As seen in FIG. 39, from distal end 678 to proximal end 680, stem 630 comprises a pair of feet, commonly numbered 682, affixed to extended legs 684 for sensing syringe face 32. Proximal from legs 684 is a bulbous section 686 sized and shaped to occlude hole 670 of piston 610. A proximal face 688 of section 686 is sized and shaped in complimentary form to frustoconically shaped opening 672 such that when in contact therewith proximally directed flow is inhibited.

A second bulbous section 690 is sized and shaped to occlude hole 658 when disposed therein. More proximal than section 690 are two elongated legs, commonly numbered 692. A pair of anchoring feet, each numbered 694, are affixed to legs 692. Feet 694 extend outward to be anchored in groove 676 when disposed thereat.

Flush relief valve piston 640 comprises a distal cavity 696 which is sufficiently large in diameter to permit facile displacement of feet 694 therein. Proximal to cavity 696, piston 640 comprises a hole section 698 of restricted size, reason for which is clearly disclosed hereafter. Proximally disposed relative to section 698 is a hollow tube 700. Together cavity 696, section 698 and tube 700 provide a continuous pathway 702 through piston 640.

Stem 650 comprises sensor legs, commonly numbered 704, a bulbous section 706 and guide fins 708. Section 706 is sized and shaped to occlude hole of section 698 when resident therein. Note that stems have open ducts, commonly numbered 710, which provide pathways for fluid flow.

An assembled and actuated pressure-actuated valve 720 is seen in FIG. 41A. Actuation method is fully disclosed hereafter. When actuated, bulbous section 690 is disposed out of and proximal to hole 658. When fluid flow is in direction of arrow 722 fluid force displaces stem 630 in direction of arrow 722 opening a gap which permits flow between proximal face 688 of section 686 and opening 672. When fluid flow is in direction of arrow 724 (as illustrated in FIG. 41B), stem 630 is displaced proximally to close the gap between face 688 and opening 672. Thus, so displacing stem 630 provides a check valve against proximal flow within pressure-actuated valve 720.

A fully assembled and filled mixing syringe with flush 600 is seen in FIG. 42. Pressure-actuated valve 720 is in a pre-actuation state, stem 630 being disposed to occlude hole 658. Also, an assembled flush valve 730 is disposed with stem 650 occluding hole 698. In this manner, barrel 10', valve 720, valve 730 and plunger rod piston 54 are disposed to provide three disparate chambers 732, 734, 736 enclosed within barrel 10'. In this example, chamber 732 contains a solid dose material, chamber 734 contains a diluent 742 and chamber 736 contains flushing liquid 746.

As illustrated in FIG. 43, applying force against plunger assembly 50' in direction of arrow 748 increases pressure in barrel 10' which acts to displace piston 610 distally, opening valve 720 to permit fluid flow from chamber 734 into chamber 732. Note that valve 720 function as disclosed in FIGS. 41A, 41B and 42 permit transfer of diluent 742 into chamber 732 to form mixture 750, as seen in FIG. 44. Sequential application of force in direction of arrow "pumps" substantially all diluent 742 from chamber 734.

Once piston 640 is displaced into contact with piston 630, further force in direction of arrow 754 displaces piston 630 against piston 620 to further reduce dead space, as seen in FIG. 45.

With cap 40 removed from barrel 10', barrel 10' of flushing syringe 600 is oriented vertically, as seen in FIG. 46 for purging of gas per conventional syringe handling technique. (i.e. Simply depressing plunger assembly 50' in direction of arrow 756 forces gas from syringe barrel 10'. Once purged of gas, syringe 600 is ready for mixture 750 (the dose) before flush 746 delivery as seen in FIG. 47. By pressing on plunger stem assembly 50' in direction of arrows 758 and 760 (see FIG. 48) mixture 750 (the dose) is completely delivered as piston valve 720 is displaced to evacuate chamber 732. At such time, section 686 is displaced through hole 670 of valve piston 610, occluding flow there through until chamber 732 is emptied.

Displacement of stem 630 not only opens ducts 710 to permit fluid flow there through, but extending of feet 680 proximally, also displaces stem 650 of piston valve 640 to permit flushing fluid flow from chamber 736, as seen in FIG. 48. Note, in FIG. 49, that displacement of plunger rod assembly 50' is stopped by collision of plunger rod assembly 50' wings 770 against barrel 10'. The effect of so stopping obviates reflux in a connecting catheter and assure gas 780 is not delivered from chamber 736.

Figure 51:
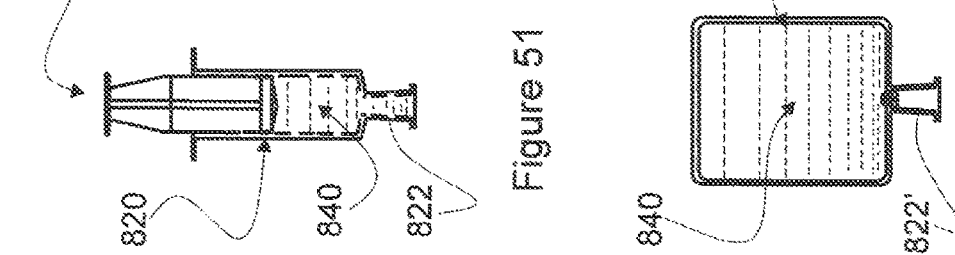
Figure 52:
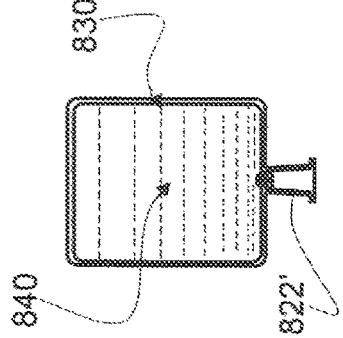

A third embodiment of a system 800 for a mixing syringe with flush is seen in FIGS. 33-38. System 800 comprises a dual chamber syringe 810 (seen in FIG. 50) and a separate vessel for providing a mixing liquid source, examples of which are a pre-filled syringe 820 with a female luer fitting 822 (seen in FIG. 51) and a blow molded pouch 830 with a female luer fitting 822' (seen in FIG. 52). A similar system is disclosed in Thorne '343 (see FIG. 36). Of course vessels with other than female luer fitting can be used within the scope of the invention, but a female luer fitting directly communicates with a male luer fitting of syringe 810, requiring no additional connecting interfaces. Each vessel seen in FIGS. 51 and 52, by example, contains a diluent 840 for delivery to syringe 810.

As seen in FIG. 50, syringe 810 comprises a distal chamber 842 and a proximal chamber 844 separated by a piston valve 845. Make-up and operation of syringe 810 is fully disclosed in Thorne '343. Distal chamber 842 contains a lyophilized quantity of material 846 to be mixed with diluent 840. Of course, any material which is to be mixed with diluent 840 may be resident in distal chamber 842. Proximal chamber 844 contains a flushing fluid 848.

Figure 55:
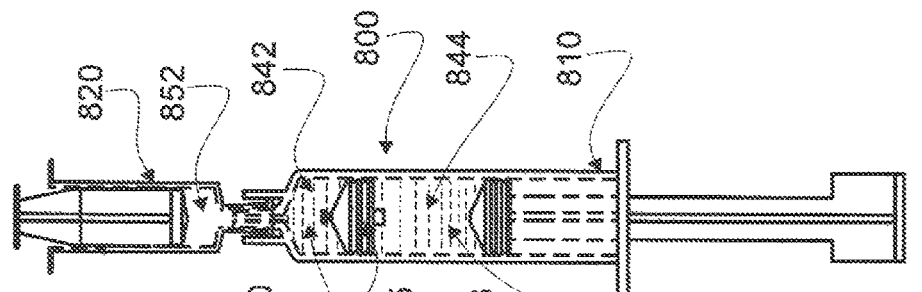
FIG. 55 is a schematic representation of the system seen in FIG. 54 with gas displaced from the dual chamber syringe.
Figure 54:
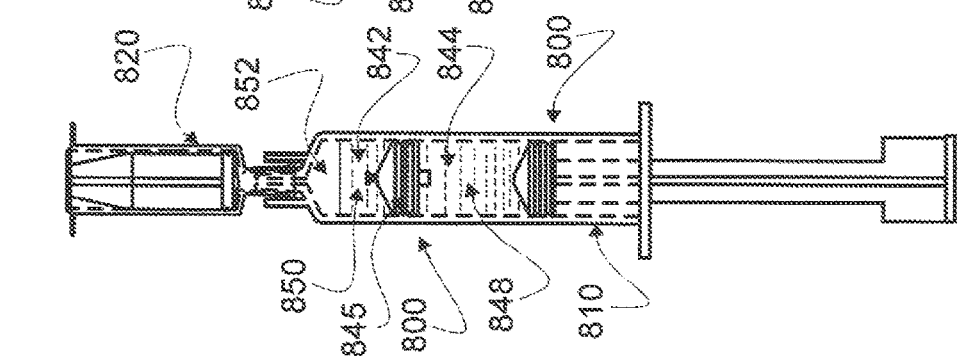
FIG. 54 is a schematic representation of the system seen in FIG. 53 with fluid provided in the pre-filled syringe displaced into the dual chamber syringe for mixing.
Figure 53:
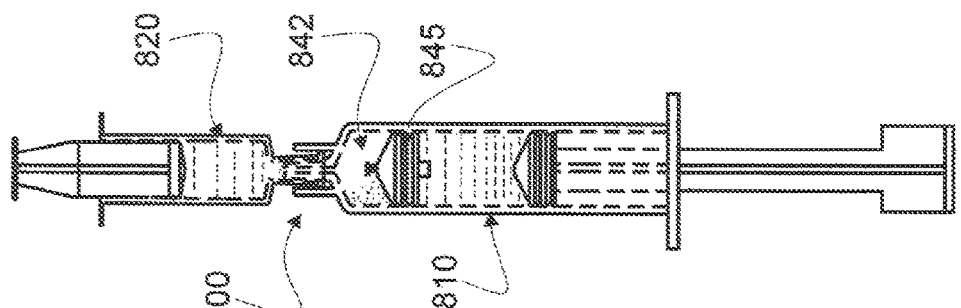
FIG. 53 is a schematic representation of a system comprising the dual chamber syringe seen in FIG. 50 and pre-filled syringe seen in FIG. 51.

To accomplish mixing in chamber 842, by example, pre-filled syringe 820 is affixed to syringe 810 as seen in FIG. 53. Diluent is displaced into chamber 842 to provide a mixture 850 and gas 852 in chamber 842, as seen in FIG. 54. Note that gas 852 may be purged from chamber 842 into pre-filled syringe 820, as seen in FIG. 55. As is well known in syringe medical delivery art, syringe may be detached from syringe 810 and syringe 810 capped or otherwise directly used for delivery of mixture 850 followed by flush 848 (which is resident in chamber 844).

The second and third mixing syringe with flush embodiments, referenced hereafter as triple chamber and dual chamber in Table I, respectively, are both designated as being preferred, but for different reasons. The following Table I summarizes mixing syringe device characteristics permitting a basis for preference for selecting use and application of one over the other.

TABLE I

Comparison of triple chamber mixing with flush syringe vs. dual chamber mixing with flush syringe using diluent vessel

| Item | Dual chamber | Triple chamber | Comment |
| --- | --- | --- | --- |
| Usable volume for liquid storage | Larger | | Triple chamber requires space for an extra valve |
| Steps to mix drug | Fewer steps | | Displacement of diluent must be "pumped" in triple chamber |
| Self-contained? | No: Two vessels | Yes | Yields simpler package, handling |
| Device complexity | Single valve | Three valves | One valve, rather than three |
| Packaging complexity | Greater | Less | Dual chamber device requires a syringe and a diluent vessel in a convenience kit package |
| Force to dispense drug | Less | Greater | Force required to displace four pistons vs. two pistons |
| Syringe pump compatibility | Better | | Less likely to excite occlusion alarm |

The inventions disclosed herein may be embodied in other specific forms without departing from the spirit or essential characteristics thereof. The present embodiments are therefore to be considered in all respects as illustrative and not restrictive, the scope of these inventions being indicated by the appended claims rather than by the foregoing description, and all changes which come within the meaning and range of equivalency of the claims are therefore intended to be embraced therein.

Valve Piston Canting and Shrinkage Considerations

As disclosed supra, a goal of keeping proximally and distally disposed materials disparate in a syringe barrel by a piston valve is challenged by changes which may occur in compressive set of the valve piston, ballooning of the valve piston and stiction occurring between the valve piston and associated syringe wall. It has been discovered that some butyl materials compress when disposed within a syringe barrel. For this reason, dimensions such pistons may be uncontrollably affected and shrinkage can yield pistons which no longer operate robustly to maintain chambers disparate in syringe barrels.

Stiction is a common occurrence in syringes which are left unused for an extended period. Stiction when not occurring uniformly about a valve piston can, under stress of an excessive pressure differential about the piston, cause piston deformation. Such deformation can cause rings of a piston to be displaced from contact with a barrel inner surface and result in blow-by. Even though such displacement may only be for an instant while piston material decompresses, fluid under pressure is free during that instant to cause blow-by. Another deformation is ballooning which tends to bulge the distal face of the piston with an associated deformation of the piston body due to pressure differential across the piston.

Reference in now made to FIGS. 56-63A. A piston valve 900, similar to the piston valve 845 seen in dual chamber syringe 810 in FIGS. 50 and 53-55, is seen in FIG. 56. Piston valve 900 comprises a valve piston 910 having a plurality of barrel interfacing rings, a distal ring 912, a medial ring 914 and a proximal ring 916 which are sized and shaped to interface with and wipe material from inner barrel surface 30 (see FIG. 1) and keep that matter disposed on opposite sides of piston valve 900 disparate when disposed within a barrel 10 (see FIG. 60).

Figure 62A:
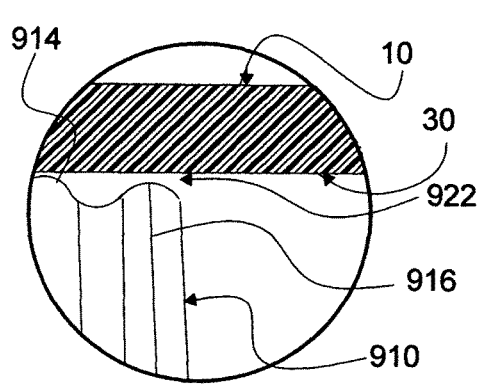
FIG. 62A is a replication of a circled area in FIG. 62 magnified for a clearer view of details.
Figure 62:
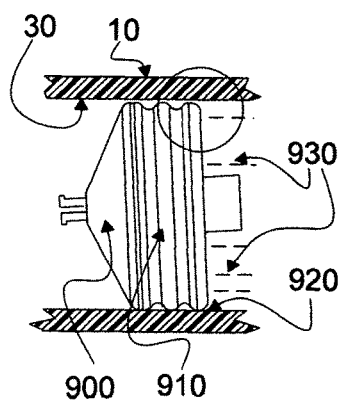
FIG. 62 is a side elevation of the piston valve in the barrel section seen in FIG. 60 canted with rings of the valve displaced from contact with the barrel.

When stiction occurs as portrayed, by example, in FIG. 62, due to immovability along a barrel inner surface 30 at a site 920 and a pressure differential exerted upon upstream fluid 930 to break stiction, a resulting distortion of valve piston 910 as seen in FIG. 62 can result. Better seen in FIG. 62A, rings such as ring 916 and 914 can momentarily break away, again by example, from inner barrel wall 30 to threaten or cause blow-by by opening a space 922 between rings (e.g. 916 and/or 914). Inventors have observed such to occur in post sterilized dual chamber syringes.

To attempt to offset such an occurrence, diameter of a proximal ring 916' can be enlarged to withstand distorting pressurized fluid forces about a valve piston 910' with an air buffering cavity 932, as seen in FIG. 56A. While such an increase in diameter is effective under conventional use, effects of compression set and stiction may counter the increase in diameter resulting in blow-by.

To effectively neutralize effects of stiction (and other negative results associated with blow-by), a proximally disposed barrier 940 is affixed to valve piston 910" of piston valve 900" seen in FIGS. 57, 58 and 59. The width dimensions of side wall 942, while seen to extend away from ring 916 approximately the same distance as tube 700 (which opens to a liquid only zone), may be sized to provide different wall 30 interaction in differently sized syringes.

Figure 63A:
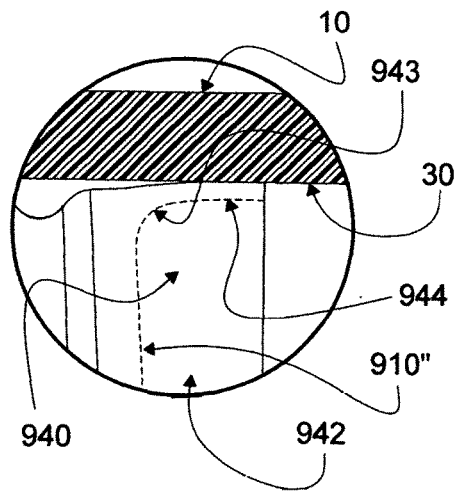
FIG. 63A is a replication of a circled area in FIG. 63 magnified for a clearer view of details.
Figure 63:
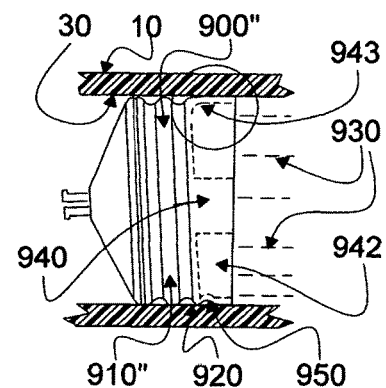
FIG. 63 is a side elevation of the piston valve in the barrel section seen in FIG. 61 canted with rings of the valve displaced from contact with the barrel but with a seal in place provided by the barrier.

As seen in FIG. 61, barrier 940 is sized and shaped to wipe lightly circumferentially upon surface 30 of barrel 10. When stiction occurs at an exemplary site 920 due to pressure exerted upon upstream fluid 930 (seen in FIG. 63), angular deflection of valve piston 910 tends to force exterior side wall 942 of barrier 940 into greater tension against wall 30. Further, as seen in FIGS. 63 and 63A, incompressibility of material of valve piston 910" tend to force more proximal portions 944 of wall 942 into an orthogonal relationship with surface 30, perhaps resulting in buckling barrier 942 as seen at locale 950 in FIG. 63. Such events cause a seal to be made (a "make") before deflection of valve piston 910 causes proximal ring 916 to be displaced from contact (a seal "break", providing a make before break seal condition).

Figure 56B:
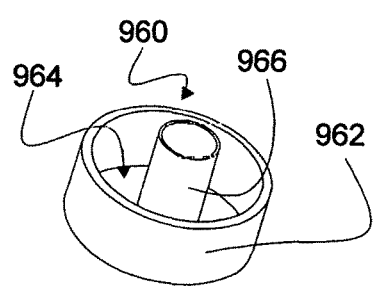
FIG. 56B is a perspective of a seal/support which is sized and shaped to fit securely within a cavity of the piston valve as seen in FIG. 56.

To deter canting and effects of ballooning, a seal/support 960 can be provided as seen in FIG. 6B. As seen in FIG. 56B, seal/support 960 comprises a support ring 962 and a face plate 964. In addition, a proximally extending tube 966 may be provided for being disposed about tube 700 (see FIG. 59). Ring 962 and face plate 964 are sized and shaped to closely fit against corresponding surfaces of valve piston 910" or 910 (see FIG. 56). As such seal/support 960 acts to stabilize valve piston rings (as examples, 912, 914 and 916) against canting while providing a seal against communicating pressure against distal portions of valve piston 910 or 910" (when disposed as seen in FIG. 59).

Reference is now made to FIGS. 64 and 65 wherein a valve pistons 970 and 972, respectively are seen. Each piston 970 and 972 comprises rings 912, 914 and 916, similar to valve piston 910, see FIGS. 56 and 56A. Further each piston 970 and 972 comprises a frustoconical distal fluid interfacing surface 910", as seen in FIG. 58. In addition, each piston 970 and 972 comprises a pathway 702', which is similar to pathway 702 seen in FIG. 40. When obstructed by an appropriately sized stem, similar to a stem 650 seen in FIG. 42, pathway 702' is closed to fluid flow.

Referring now to FIG. 64, valve piston comprises a proximally exposed, frustoconically shaped surface 974. A barrier ring 940', similar to barrier ring 940 seen in FIGS. 58 and 59, extends proximally from surface 974. Note that barrier ring 940' comprises a cut ring 941 which provides a parting site for separating valve piston 970 from a mold base.

Also extending proximally is a tube 700', which is similar in internal structure to tube 700, see FIG. 40. It should be noted that, when a positive pressure differential is applied in direction of arrow 980, deformation of piston 970 tends to internally increase pressure upon (having therefore increased effective diameter of) ring 912. Similarly, a positive pressure differential applied in direction of arrow 980' deforms piston 970 at surface 974 with increased force being driven toward ring 916 by a similar internal increase in pressure. Thus, proximally exerted positive pressure acts to close ring leakage, rather than open a pathway as seen in FIG. 62A. For secondary proximal seal protection, barrier 940' provides leakage obstruction in the same manner as barrier 942, seen in FIG. 63A. It should be noted that a cavity 976 for gas storage is limited by surface 974.

Valve piston 972, is substantially the same as piston 970 except that proximal surface 974' is further inset than surface 974. For piston 972, surface 974' is aligned with ring 914 for the same function and purpose surface 974 is aligned with ring 916. The further inset of surface 974 increases capacity of gas storage cavity 976' to a greater volume than the capacity of cavity 976.

What is claimed and desired to be secured by Letters Patent is:

1. A syringe apparatus for mixing and dispensing medical fluids, said apparatus comprising:
    a syringe comprising a conventional hollow barrel having an elongated internal cylindrical surface of substantially constant cross section, said barrel surface comprising an open proximal end and a distal end having a closed interior about an orifice through which fluid is transferred, and a plunger rod and piston combination, said combination being disposed to be displaced within said barrel by application of force in a predetermined direction against said plunger rod thereby imposing predetermined differential pressures for displacing fluid within said barrel;
    a removable cap which, in combination with said plunger rod piston, fully confine all fluid and material previously stored within said syringe barrel between said piston and said cap;
    a bi-stable, displaceable, pressure-actuated piston valve disposed within said barrel between said plunger rod piston and said distal end to initially provide a more proximal chamber disposed between said plunger rod and piston valve as a closed container for a first volume of liquid and a more distal chamber disposed between the distal end and piston valve as a closed container for a second predetermined volume of matter, said piston valve comprising an initial state which is closed and a second state which is open as a result of application of force against said plunger rod to produce a predetermined amount of pressure inside said barrel, thereby establishing conditions for changing the state of the piston valve which are contrary to inadvertent valve opening;
    a communicating fluid pathway between said chambers which is available for fluid flow when said piston valve is disposed in an open state;
    gas disposed within the more distal chamber for facilitating displacement of liquid from the more proximal chamber into the more distal chamber; and
    additional valving which is permissive to fluid flow from the more proximal chamber to the more distal chamber when insertive force is applied to said plunger rod and which is obstructive to fluid flow from the more distal chamber to the more proximal chamber.

2. A syringe apparatus according to claim 1 wherein said additional valving comprises a check valve which is permissive to fluid flow only from the proximal chamber into the distal chamber upon application of force upon the plunger rod to thereby compress gas in the distal chamber, said gas, when compressed, operating to displace said piston valve proximally.

3. A medical syringe apparatus according to claim 1 wherein said piston valve comprises two separate piston parts, a distally disposed valve part and a proximally disposed mooring part and a valve stem.

4. A medical syringe apparatus according to claim 3 wherein said valve part comprises a through hole which is part of said pathway and which comprises a throat section having a diameter sized for occlusion by a bulbous section of the valve stem.

5. A medical syringe apparatus according to claim 4 wherein said stem comprises an enlarged bulbous section which, when displaced into said throat section provides a plug against fluid flow, thereby keeping the chambers disparate.

6. A medical syringe apparatus according to claim 5 wherein said mooring part comprises a communicating opening whereby fluid forced through said opening operates to displace said valve part, while closed, distally.

7. A medical syringe apparatus according to claim 6 wherein said mooring part comprises a stay and said stem comprises an anchor in a combination which retards stem distal displacement relative to said mooring part.

8. A medical syringe apparatus according to claim 1 further comprising an additional valve for further dividing said barrel by which the proximal chamber is divided into a middle chamber and a most proximal chamber wherein flush solution is stored to provide a flush after dispensing a dose from the distal chamber where diluent is dispensed from the middle chamber and mixed with matter in the distal chamber.

9. A medical syringe apparatus according to claim 8 wherein said stem comprises a predetermined distance between said mooring part and said bulbous section such that when force is applied to said plunger rod to displace liquid from the proximal chamber to force said valve part distally, relative to said mooring part, said bulbous section is displaced from said throat, thereby opening said pathway due to application of a predetermined pressure for a predetermined period of time, the open state being visibly evident by increased separation of said parts.

10. A medical syringe apparatus according to claim 8 wherein said additional valve comprises a displaceable obstruction within a flow path which, when displaced, opens said additional valve to fluid flow from the most proximal chamber.

11. A medical syringe apparatus according to claim 8 wherein said valve stem and said displaceable obstruction comprise a sensor which acts to displace said obstruction and open said additional valve when the distal chamber is emptied.

12. A medical syringe apparatus according to claim 8 wherein said additional valve comprises an elongated closed pathway from said valve to a liquid only zone in the most proximal chamber which physically causes only liquid to be delivered from the most proximal chamber.

13. A medical syringe apparatus according to claim 8 wherein said barrel and said plunger rod in combination comprise a stop which limits the amount of liquid volume dispensed from the most proximal chamber and negates reflux at the end of the most proximal chamber dispensing cycle.

14. A method for containing and mixing two materials enclosed within a syringe apparatus comprising the following steps:

providing:
1) a syringe comprising a conventional hollow barrel having an elongated internal cylindrical surface of substantially constant cross section, said barrel surface comprising an open proximal end and a distal end having a closed interior about an orifice through which fluid is transferred, and a plunger rod and piston combination, said combination being disposed to be displaced within said barrel by application of force in a predetermined direction against said plunger rod thereby imposing predetermined differential pressures for displacing fluid within said barrel;
2) a removable cap which, in combination with said plunger rod piston, fully confines all fluid and material previously stored within said syringe barrel between said piston and said cap;
3) a bi-stable, displaceable, pressure-actuated piston valve disposed within said barrel between said plunger rod piston and the distal end to initially provide a more proximal chamber disposed between said plunger rod and piston valve as a closed container for a first volume of liquid and a more distal chamber disposed between the distal end and piston valve as a closed container for a second volume comprising a predetermined amount of matter, said piston valve comprising an initial state which is closed and a second state which is open as a result of application of force against said plunger rod to produce a predetermined amount of pressure inside said barrel for a predetermined period of time, thereby establishing conditions for changing the state of the piston valve which are contrary to inadvertent valve opening;
4) a communicating fluid pathway between said chambers which is available for fluid flow when said piston valve is disposed in an open state;
5) structure which is conducive to fluid flow from the proximal chamber to the distal chamber when positive force is applied to said plunger rod; and
6) gas disposed within the distal chamber for facilitating displacement of liquid from the proximal chamber into the distal chamber;

with said cap disposed to close the distal end, applying compressive force against said plunger rod for sufficient time to pressurize liquid in the proximal chamber and thereby changing the state of said piston valve;

continuing to apply intermittent force against said plunger rod to dispense liquid from the proximal chamber into the distal chamber thereby establishing conditions for mixing of liquid and matter.

15. A method for containing and mixing two materials enclosed within a syringe apparatus according to claim 14 comprising an additional step of providing an additional valve for further dividing said barrel in which the proximal chamber is divided into a middle chamber and a most proximal chamber wherein flush solution is stored to provide a flush after dispensing a dose from the distal chamber where diluent is dispensed from the middle chamber and mixed with matter in the distal chamber.

16. A method for containing and mixing two materials enclosed within a syringe apparatus according to claim 14 comprising the following additional step:

when distal chamber dispensing is complete, continuing to apply pressure against said plunger rod to dispense flush.

17. A mixing syringe with flush system comprising:

a syringe comprising a conventional hollow barrel having an elongated internal cylindrical surface of substantially constant cross section, said barrel surface comprising an open proximal end and a distal end having a closed interior about an orifice associated with a male luer fitting through which fluid is transferred in medical procedures, and a plunger rod and piston combination, said combination being disposed to be displaced within said barrel by application of force in a predetermined direction against said plunger rod thereby imposing predetermined differential pressures for displacing fluid within said barrel;

a piston valve disposed within said barrel, said valve being normally disposed within said barrel in a closed state and only actuated to an open state by impact of said valve against said proximal end of said barrel, said barrel being initially divided into a distally disposed mixing chamber and a proximally disposed flush containment chamber by said valve; and a pre-filled vessel containing mixing solution, said pre-filled vessel comprising a fluid dispensing orifice comprising a female luer connector.

* * * * *